(12) United States Patent
Carabe-Fernandez et al.

(10) Patent No.: US 11,213,699 B2
(45) Date of Patent: Jan. 4, 2022

(54) METHODS AND SYSTEMS FOR PARTICLE BASED TREATMENT USING MICRODOSIMETRY TECHNIQUES

(71) Applicant: The Trustees of the University of Pennsylvania, Philadelphia, PA (US)

(72) Inventors: Alejandro Carabe-Fernandez, Philadelphia, PA (US); Alejandro Bertolet Reina, Philadelphia, PA (US); Miguel Antonio Cortes-Giraldo, Seville (ES)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 16/435,057

(22) Filed: Jun. 7, 2019

(65) Prior Publication Data

US 2020/0384290 A1 Dec. 10, 2020

(51) Int. Cl.
*G16H 20/40* (2018.01)
*A61N 5/10* (2006.01)

(52) U.S. Cl.
CPC ......... *A61N 5/1039* (2013.01); *A61N 5/1031* (2013.01); *G16H 20/40* (2018.01); *A61N 2005/1087* (2013.01)

(58) Field of Classification Search
CPC ............... A61N 5/1039; A61N 5/1031; A61N 2005/1087; G16H 20/40
USPC .......................................................... 703/2
See application file for complete search history.

(56) References Cited

U.S. PATENT DOCUMENTS

| | | |
|---|---|---|
| 2006/0285640 A1 | 12/2006 | Nizin et al. |
| 2010/0288946 A1 | 11/2010 | Honda et al. |
| 2017/0028219 A1 | 2/2017 | Pu et al. |
| 2019/0111281 A1* | 4/2019 | Wulff ..................... G16H 20/40 |

OTHER PUBLICATIONS

Radhe Mohan, Christopher R. Peeler, Fada Guan, Lawrence Bronk, Wenhua Cao, David R. Grosshans, "Radiobiological Issues in proton therapy", (2017) Acta Oncologica 56:11, 1367-1372, DOI 10.1080/0284186X.2017.1348621. pp. 1367-1373.*
Keyvan Jabbari, "Review of Fast Monte Carlo Codes for Dose Calculation in Radiation Therapy Treatment Planning" Journal of Medical Signals and Sensors, Jan.-Apr. 2011, 1(1): pp. 73-86.*
I, Chu; S. Cho, E Kim, Y, Song, J Shin, W, Jung, "Modeling the Biophysical Effects in a Carbon Beam Delivery Line Using Monte Carlo Simulations" Journal of the Korean Physical Society, vol. 69, No. 5 Sep. 2016, pp. 868-874.*
Mohan R, Peeler CR, Guan F, Bronk L, Cao W, Grosshans DR. Radiobiological issues in proton therapy [published correction appears in Acta Oncol. Jan. 2019;58(1):132], Acta Oncol. 2017;56(11):1367-1373. doi:10.1080/0284186X.2017.1348621.*
Jabbari K. Review of fast monte carlo codes for dose calculation in radiation therapy treatment planning. J Med Signals Sens. 2011;1(1):73-86.*

(Continued)

*Primary Examiner* — Saif A Alhija
(74) *Attorney, Agent, or Firm* — BakerHostetler

(57) ABSTRACT

Methods and systems are described for determining particle treatment information. An example method may comprise determining a segment-averaged dose-averaged restricted linear energy transfer. The linear energy transfer may be determined by accounting for variations in segment length of paths of particles in a site.

20 Claims, 23 Drawing Sheets

(56) References Cited

OTHER PUBLICATIONS

Belli et al., "RBE-LET relationships for cell inactivation and mutation induced by low energy protons in V79 cells: Further results at the LNL facility", Int J Radiat Biol., 1998, 74(4), 501-509.
Berger MJ, Coursey JS, Zucker MA, Chang J. Stopping-Power; Range Tables for Electrons, Protons, and Helium Ions I NIST. NIST Standard Reference Database 124. https://www.nist.gov/pml/stopping-power-range-tables-electrons-protons-and-helium-ions. Published 2017. Accessed Dec. 19, 2018.
Bernal MAA, Bordage MCC, Brown JMCMC, et al. Track structure modeling in liquid water: A review of the Geant4-DNA very low energy extension of the Geant4 Monte Carlo simulation toolkit. Phys Medica. 2015;31(8):861-874.
Bethe H. Zur Theorie des Durchgangs schneller Korpuskularstrahlen <lurch Materie. Ann Phys. I 930;397(3):325-400.
Chen J, Kellerer AM, Rossi HH. Radially restricted linear energy transfer for high-energy protons: a new analytical approach. Radiat Environ Biophys. 1994;33(March): 181-187.
Cucinotta FA, Nikjoo H, Goodhead DT. Model for Radial Dependence of Frequency Distributions for Energy Imparted in Nanometer Volumes from HZE Particles, Radiat Res. 2000;153(4):459-468.
Fager et al., "Linear Energy Transfer Painting With Proton Therapy: A Means of Reducing Radiation Doses With Equivalent Clinical Effectiveness", Int J Radiat Oneal, 2015, 91(5), 1057-1064.
Grassberger et al., "Elevated LET components in clinical proton beams", Phys Med Biol., 2011, 56(20), 6677-6691.
Grun et al., "Is the dose-averaged LEI a reliable predictor for the relative biological effectiveness?", Med Phys., 2018.
Incerti S, Baldacchino G, Bernal M, et al. The Geant4-DNA project. Int J Model Simulation, Sci Comput. 2010;1(2):157.
Incerti S, Ivanchenko A, Karamitros M, et al. Comparison of GEANT4 very low energy cross section models with experimental data in water. Med Phys. 2010;37(9):4692-4708.
Incerti S, Kyriakou I, Bemal MA, et al. Geant4-DNA example applications for track structure simulations in liquid water: A report from the Geant4-DNA Project. Med Phys. 2018;45(8):e722-e739.
Kellerer A Considerations on the random traversal of convex bodies and solutions for general cylinders. Radiat Res. 1971;47(2):359-376.
Kellerer AM. Chord-Length Distributions and Related Quantities for Spheroids. Radiat Res. 1984;98(1):425-437.
Kellerer AM. Microdosimetry and Theory of Straggling. In: Panel on Biophysical Aspects of Radiation Quality. ; 1968.
Kellerer, "Criteria for the Applicability of LET", Radiat Res., 1975, 63(2), 226-234.
Kellerer, Fundamentals of microdosimetry. In: Kase KR, Bjamgard BE, Attix FH, eds. The Dosimetry of Ionization Radiation. vol. I. Academic Press, Inc.; 1985:77-162.

Newhauser WD, Zhang R. The physics of proton therapy. Phys Med Biol. 2015;60(8):RI55-R209.
Paganetti, "Relative biological effectiveness (RBE) values for proton beam therapy. Variations as a function of biological endpoint, dose, and linear energy transfer", Phys Med Biol., 2014, 59(22), R419-R472.
Peeler et al., "Clinical evidence of variable proton biological effectiveness in pediatric patients treated for ependymoma", Radiother Oncol., 2016, 121(3), 395-401.
Rossi HH. Interpretation of Biological Response in Terms of Microdosimetry. Ann NY Acad Sci. 1969;161(1):260-271.
Sanchez-Parcerisa et al., Analytical calculation of proton linear energy transfer in voxelized geometries including secondary protons. Phys Med Biol. 2016;61(4): 1705-1721.
Santa Cruz GA, Palmer MR, Matatagui E, Zamenhof RG. A theoretical model for event statistics in microdosimetry. I: Uniform distribution of heavy ion tracks. Med Phys. 2001,28(6):988-996.
Ulmer W, Matsinos E. Theoretical methods for the calculation of Bragg curves and 3D distributions of proton beams. Eur Phys J Spec Top. 2010;190(1):1-81.
Unkelbach et al., "Reoptimization of Intensity Modulated Proton Therapy Plans Based on Linear Energy Transfer", Int J Radiat Oneal Biol Phys., 2016, 96(5), 1097-1106.
Wilkens JJ, Oelfke U. Three-dimensional LET calculations for treatment planning of proton therapy. Z Med Phys. 2004;14(1):41-46.
Xapsos MA A Spatially Restricted Linear Energy Transfer Equation. Radiat Res. 1992;132(3):282-287.
Baratto-Roldán et al. "Abstract ID: 196 Relation between dose average linear energy transfer and dose mean lineal energy calculated for proton therapy beams off axis: A study with the Geant4 toolkit.", Phys Medica. 2017;42(2017):42-43.
Hawkins RB. A Microdosimetric-Kinetic Model for the Effect of Non-Poisson Distribution of Lethal Lesions on the Variation of RBE with LET. Radiat Res. 2003; 160(1):61-69.
Hirayama et al., An analytical dose-averaged LET calculation algorithm considering the off-axis LET enhancement by secondary protons for spot-scanning proton therapy, Medical Physics, Jul. 2018, 45(7), 3404-3416.
ICRU. Report 73. Stopping of ions heavier than Helium J Int Comm Radiat Units Meas. 2005;5(1):iii-viii.
Marsolat F, De Marzi L, Pouzoulet F, Mazal A Analytical linear energy transfer model including secondary particles: Calculations along the central axis of the proton pencil beam Phys Med Biol. 2016;61(2):740-757.
ICRU Report 36, Microdosimetry, Dec. 1983, 128 pages.
Wilkens JJ, Oelfke U. Analytical linear energy transfer calculations for proton therapy. Med Phys. 2003;30(5):806-815.
Perales et al., "Parameterising microdosimetric distributions of mono-energetic proton beams for fast estimates of yD and y," Biomed. Phys. Eng. Express, 5 (2019) 045014.

\* cited by examiner

METHODS AND SYSTEMS FOR PARTICLE BASED TREATMENT USING MICRODOSIMETRY TECHNIQUES

BACKGROUND

In radiation therapy, the absorbed dose by cells determines the probability of a cell's survival. However, the biological effectiveness of the same physical dose of particle therapy and x-rays is different[1]. In particular, in vivo experiments have shown that protons are not equally effective in the entrance region, the Bragg peak or the distal falloff region of the beam[2]. This difference in radiobiological effectiveness has been related to the increase of linear energy transfer (LET) towards the end of the proton range[3-5]. There is, therefore, an increasing interest in using LET in the optimization process of the treatment plan[6,7]. Thus, there is a need for more sophisticated techniques for optimizing treatment plans.

SUMMARY

Methods and systems are disclosed for determining treatment information. An example method can comprise determining data indicative of a particle beam to apply to an object of interest and determining imaging data associated with the object of interest. The imaging data can comprise a plurality of voxels of data. The method can comprise determining, for each of a plurality of domains in a first voxel of the plurality of voxels, a plurality of distributions for characterizing interactions of particles of the particle beam with the corresponding domain. The plurality of distributions can comprise a first distribution indicative of energy imparted in a corresponding domain due to a particle traveling in the domain. The method can comprise determining, based on the plurality of distributions and for each of the plurality of domains, first data comprising energy imparted by the particle beam to the corresponding domain. The method can comprise outputting, based on the first data, data associated with treatment of the object of interest by the particle beam.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to limitations that solve any or all disadvantages noted in any part of this disclosure.

BRIEF DESCRIPTION OF THE DRAWINGS

The accompanying drawings, which are incorporated in and constitute a part of this specification, illustrate embodiments and together with the description, serve to explain the principles of the methods and systems.

DETAILED DESCRIPTION OF ILLUSTRATIVE EMBODIMENTS

Figure 1A:
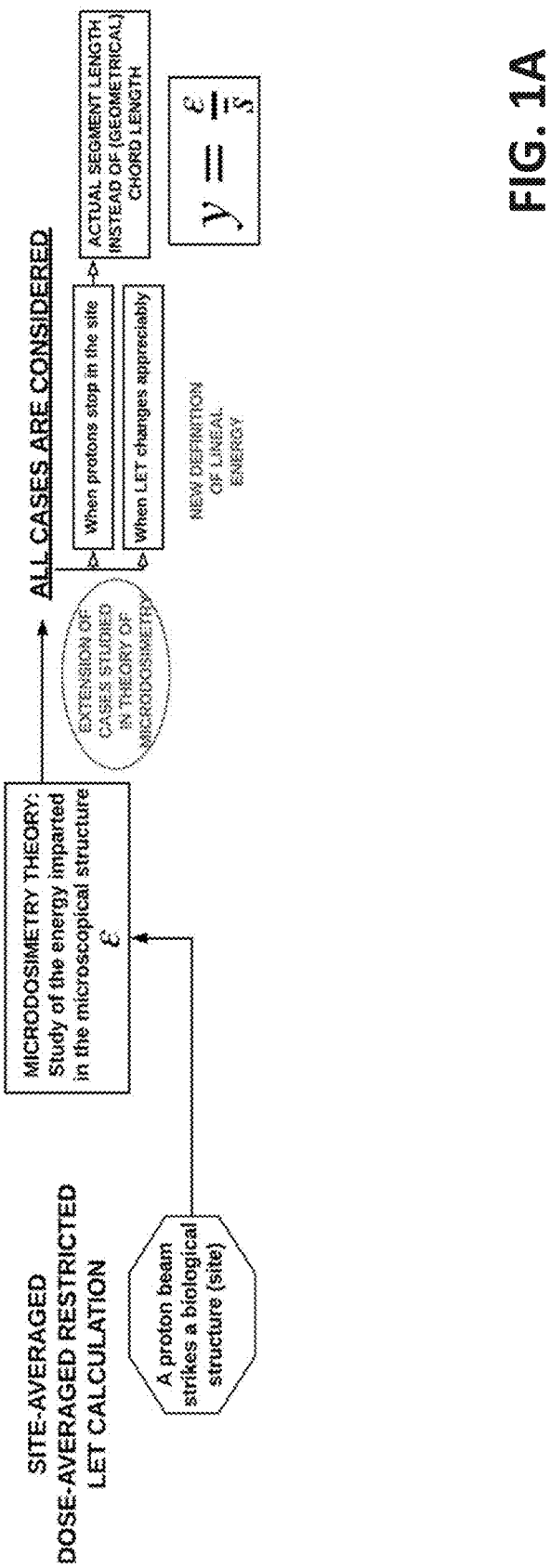
FIG. 1A shows an overview for calculating treatment information.

For at least the reasons explained the background section, there is need for an accurate and fast method to calculate LET. The present work proposes the use of generalized microdosimetry theory to calculate LET for particle beams based on the distribution of energy imparted in microscopic (and possibly biologically relevant) structures[8-10].

The present disclosure introduces the concept of segment-averaged linear energy transfer (LET) as a new approach to average distributions of LET of particle beams (e.g., proton beams) based on a revisiting of microdosimetry theory. The concept of segment-averaged LET is then used to generate an analytical model from Monte Carlo simulations data to perform fast and accurate calculations of LET distributions for particle beams.

The distribution of energy imparted by a particle beam into a representative biological structure or site is influenced by the distributions of (1) LET, (2) segment length, which is the section of the proton track in the site, and (3) energy straggling of the particle beam. The distribution of LET is thus generated by the LET of each component of the beam in the site. However, the situation when the LET of each single proton varies appreciably along its path in the site is not defined. Therefore, a new distribution can be obtained if the particle track segment is decomposed into smaller portions in which LET is roughly constant. The term "segment distribution" of LET can be the one generated by the contribution of each portion. The average of that distribution is called segment-averaged LET. This quantity is obtained in the microdosimetry theory from the average and standard deviation of the distributions of energy imparted to the site, segment length and energy imparted per collision. All this information is calculated for protons of clinically relevant energies by means of Geant4-DNA microdosimetric simulations. Finally, a set of analytical functions is proposed for each one of the previous quantities. The presented model functions are fitted to data from Geant4-DNA simulations for monoenergetic beams from 100 keV to 100 MeV and for spherical sites of 1 µm, 5 µm and 10 µm in diameter. The same approach can be employed for sites of different shapes and sizes.

The results described further herein show that the average differences along the considered energy range between calculations based on the disclosed analytical models and MC for segment-averaged dose-averaged restricted LET are −0.2±0.7 keV/µm for the 1 µm case, 0.0±0.9 keV/µm for the 5 µm case and −0.3±1.1 keV/µm for the 10 µm case, respectively. All average differences are below the average standard deviation (1σ) of the MC calculations.

The presently disclosed techniques comprise a novel approach for averaging LET for a particle beam to incorporate the effects produced by the variation of stopping power of each individual proton along microscopic biological structures. An analytical model based on MC simulations allows for fast and accurate calculations of segment-averaged dose-averaged restricted LET for particle beams, which otherwise would need to be calculated from exhaustive MC simulations of clinical plans.

The techniques and models disclosed herein can be used to calculate dose (e.g., simultaneously with LET) by using specific energy (z) instead of lineal energy (y). This calculation of dose can be performed by dividing the energy imparted by the mass of the site (e.g., instead of the segment length distribution). Using the techniques and/or models disclosed herein both averages and weighted averages for z and y can be determined. Any biologically relevant quantity derived from dose, LET, specific energy, and/or lineal energy can be determined (e.g., and output as part of a treatment planning system).

FIGS. 1A-D provide an overview of the disclosed methods and systems. FIG. 1A shows an overview for calculating treatment information. A particle beam can strike a biological structure (e.g., in a site, domain). The present technique adds a new approach to using microdosimetry to determine the energy imparted to a microscopic structure. Unlike conventional techniques, the present approach accounts for particles (e.g., protons) stopping in a site and for scenarios when LET changes in a site. The actual segment length of the particle path can be accounted for in the present technique. The microscopic quantity lineal energy y may be determined using the equation shown, which is described further herein. The lineal energy may be used to calculate the macroscopic quantity of LET.

Figure 1B:
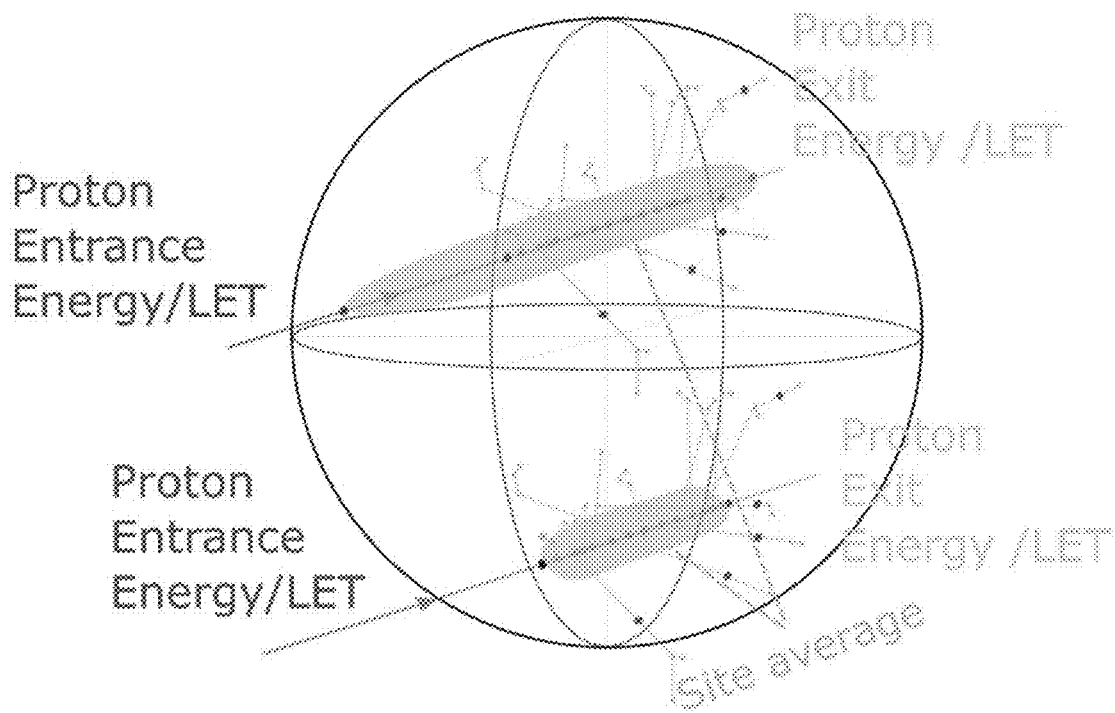
FIG. 1B shows different segment lengths for particles in a domain.

FIG. 1B shows different segment lengths for particles in a domain. An object of interest may be scanned and/or imaged to produce imaging data (e.g., or scanning data). The imaging data may be two-dimensional or three-dimensional. The imaging data may comprise a plurality of voxels (e.g., each voxel as a single unit of data). A single voxel may be subdivided into a plurality of domains (e.g., or sites). A domain (e.g., or site) may be a geometrically defined volume in a voxel. FIG. 1B shows an example domain. A domain (e.g., or site) may have one or more structures of the object of interest. The domain may be modeled as a sphere as shown, but other shapes may also be used. As shown, depending on the particle, the particle may have a different segment length. The segment length may comprise a distance a particle travels from entering the domain until coming to rest (e.g., or exiting the domain).

Figure 1C:
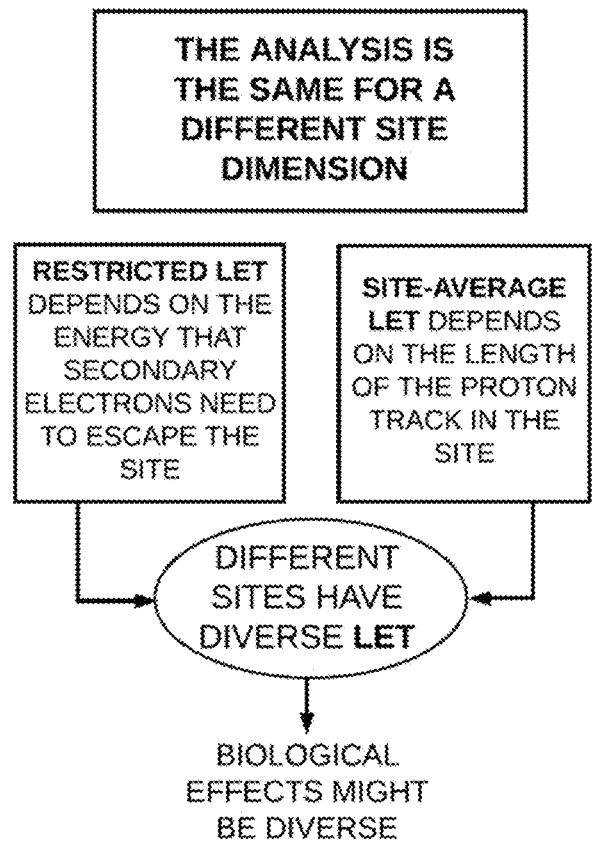
FIG. 1C shows an overview for calculating treatment information.

FIG. 1C shows an overview for calculating treatment information. Restricted LET can be dependent on the energy that secondary electrons need to escape the domain. Site-average LET can depend on the length of the proton track in the site. This figure shows an example diagram for Monte Carlo simulations with G4-DNA. The particle track (e.g., shown as a line into the sphere) may be simulated starting from the same fixed point (e.g., a source). Then, the site position may be sampled for each event at a certain point in the gray region shown, so that the relative position between the particle track and the sphere varies with the event.

Figure 1D:
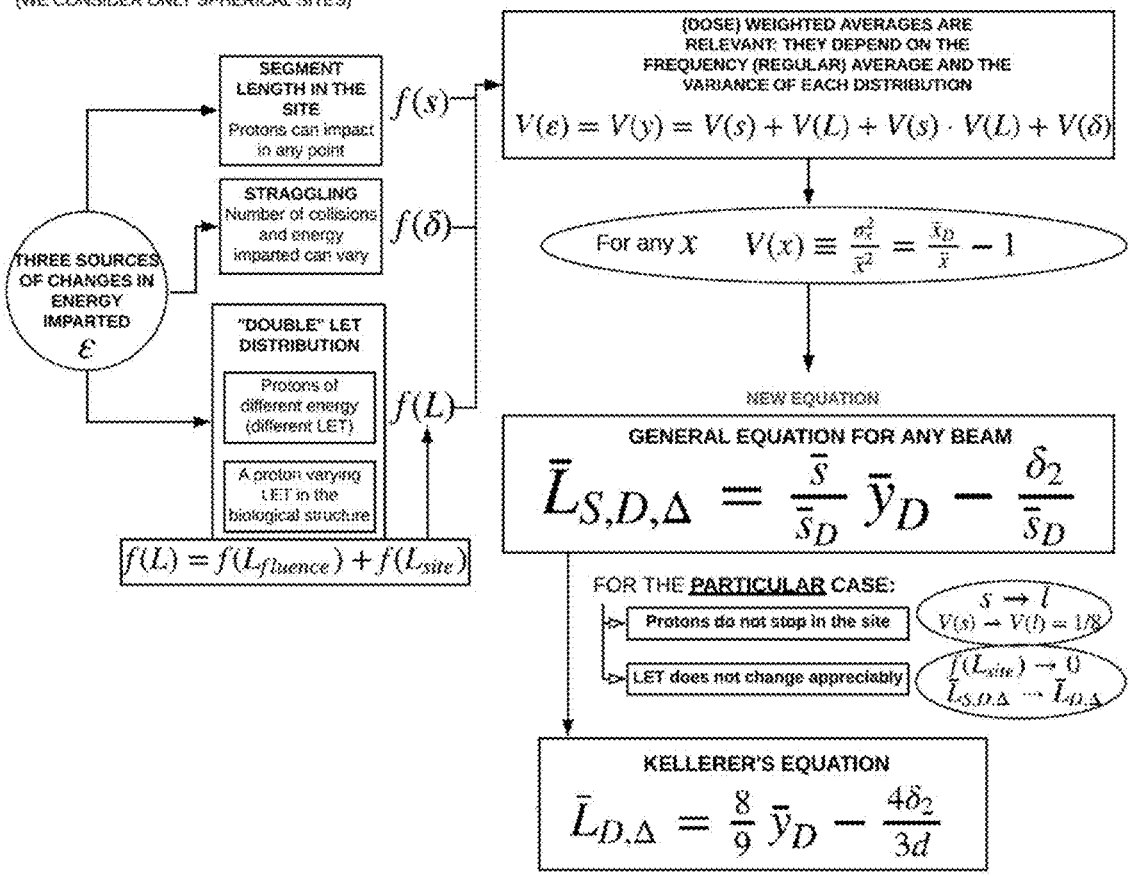
FIG. 1D shows a general technique for calculating treatment information.

FIG. 1D shows a general technique for calculating treatment information. As shown, LET can be calculated for a site/domain of dimension given by diameter d. A general equation is shown for calculating LET for any beam. Also shown, is that for the particular case of LET not changing and particles not coming to rest in a domain, Kellerer's equation may be derived.

Figure 2A:
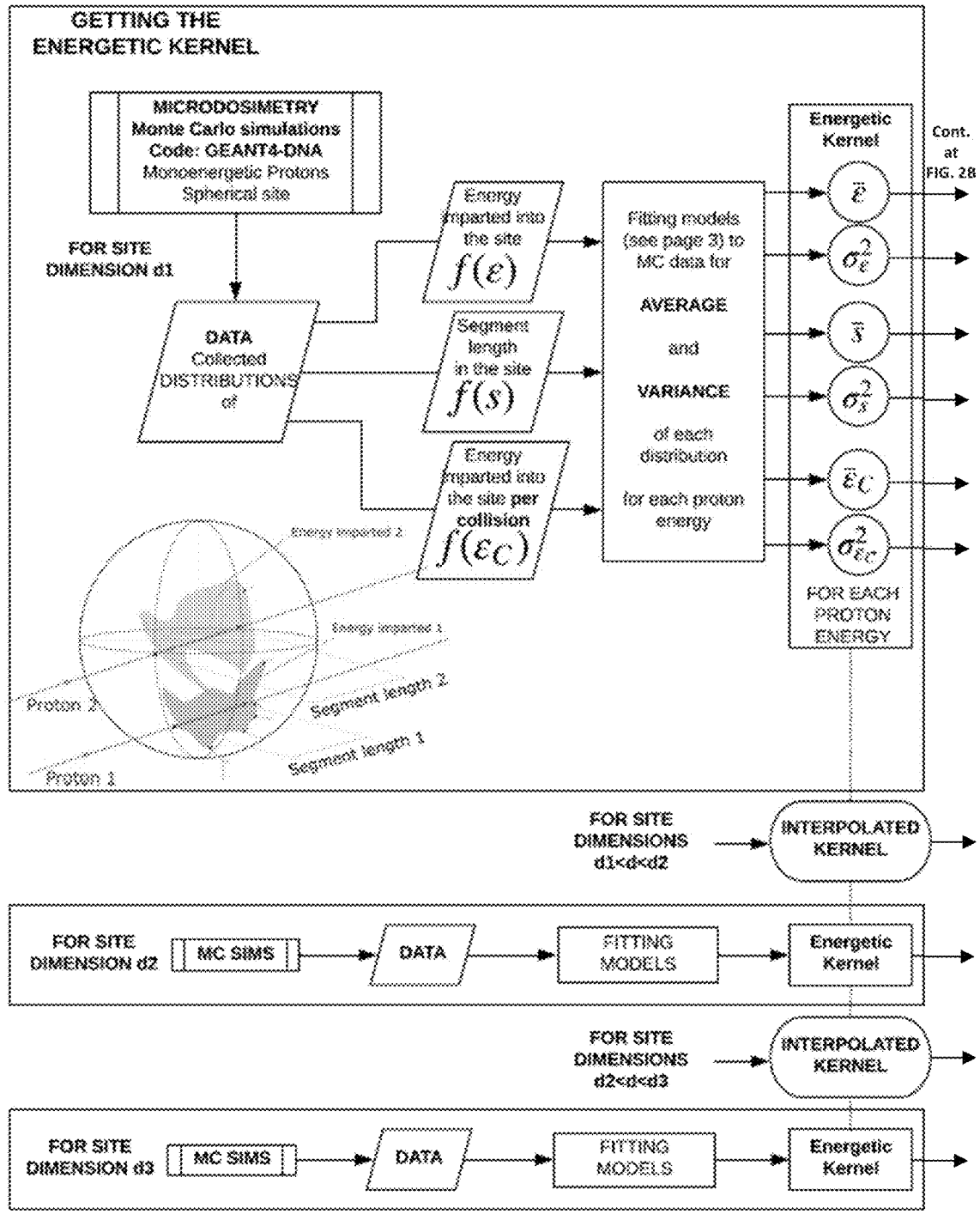
FIG. 2A shows a first part of an example technique for calculating treatment information.
Figure 2B:
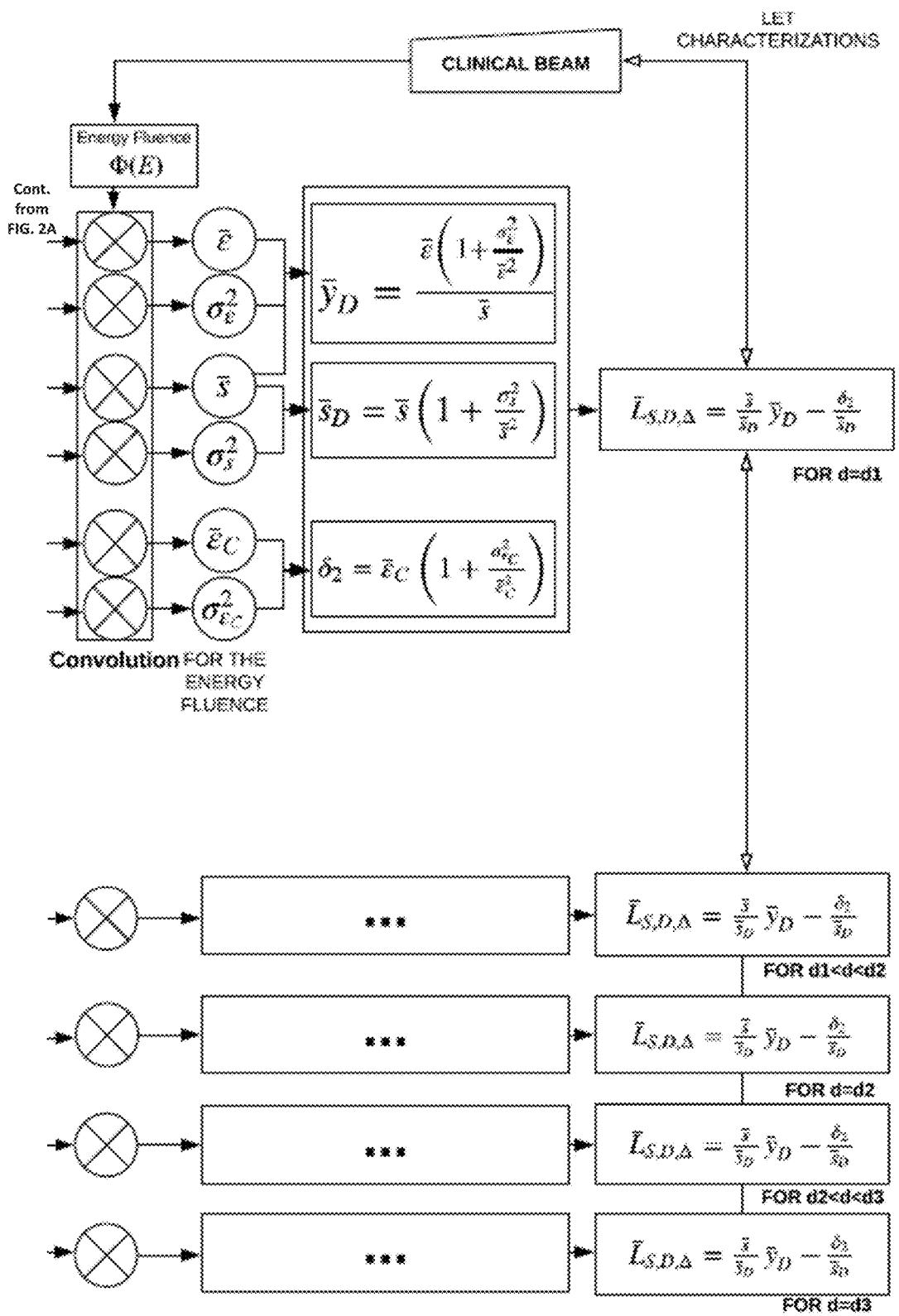
FIG. 2B shows a second part of the example technique for calculating treatment information.

FIGS. 2A-B shows an example technique for calculating treatment information. FIG. 2A shows a first part of an example technique for calculating treatment information. FIG. 2B shows a second part of the example technique for calculating treatment information. This disclosed process may be used to determine LET, dose, and/or other treatment related information. The top box shows a sample calculation for a domain (e.g., or site) of dimension dl.

Data indicative of a particle beam may be determined. The data indicative of the particle beam many comprise data from a treatment planning system, data indicative of a particle beam to be generated, and/or the like. The characteristics of the particle beam coming from the nozzle are usually given by the treatment planning system (TPS). This software comprises models for the beam that are fitted to experimental data obtained for each single treatment machine/room. Therefore, from the TPS can be obtain: (I) the number of protons coming to the patient surface, (II) the angular aperture of the beam, (III) the energy spectrum, a combination thereof, and/or the like.

The data indicative of the particle beam may comprise data specific to each voxel of patient data. The data indicative of the particle beam may comprise data indicative of a number of protons, an angular aperture of beam, and/or an energy spectrum may be determined at each voxel of a 3D patient data set.

The data indicative of the particle beam may be determined by using a simulation (e.g., or modeling) process, such as a Monte Carlo code (e.g., much faster and simpler than the microdosimetric). The simulation process can be configured to determine (e.g., for each of a plurality of domains, sites, voxels, points, and/or the like) how many protons are predicted to be delivered from a beam, how broad is predicted beam, and/or the spectrum of the beam.

A plurality of distributions may be determined. The plurality of distributions may be for characterizing interactions of particles of a particle beam with a corresponding domain (e.g., or site). The plurality of distributions can comprise a first distribution indicative of segment length of a particle path in the site, a second distribution indicative of an energy imparted in the domain due to a particle coming to rest, and a third distribution indicative of energy imparted in the site due to collisions of a particle. Determining the plurality of distributions can comprise using one or more simulations to generate the plurality of distributions. Example simulations may comprise Monte Carlo simulations, GEANT4-DNA simulations, and/or the like. GEANT4-DNA can be a particular Monte Carlo code. The simulation can comprise using random numbers to determine a value from a given range of possibilities. The simulation can consider the processes possibly occurring in the interaction particle-matter (whose relative probabilities are known) and selecting one of possibility by generating a random number. By simulating a sufficiently large number of cases (e.g., particles in a beam) the resulting distribution can provides an estimation of a real-world result. The simulation may simulate transport of particles in matter. The simulation can simulate interactions between particles and matter at a microscopic level.

An energetic kernel can be determined based on the plurality of distributions. The energetic kernel can comprise a first average of at least one of the plurality of distributions and a first variance of the at least one of the plurality of distributions. For example, an average of the distribution and a variance of the distribution can be determined for each of the plurality of distributions. This determination can be made for each proton energy of an expected particle beam.

The term "energetic kernel" indicates that the model can transform a given function of the particle energy (e.g., the energy spectrum) into another function independent of the particle energy (e.g., dose or LET) by integrating over the particle energy the product of the input and the energetic kernel (e.g., which can also be a function dependent on the particle energy). Continuing at FIG. 2B, the averages and the variances calculated (e.g., the energetic kernel) may each undergo a convolution with the energy fluence (e.g., for a particular particle beam, such as a proton beam). The results of the convolution may be used to calculate the segment-averaged dose-averaged restricted LET for a given site size/diameter. The result can be used to further refine the properties of the particle beam.

The results can be used to determine (e.g., or update a treatment plan). The treatment plan can be a plan to deliver a dose to corresponding voxels of a set of voxels in a 3D image that represent the patient. A predicted distribution of dose and/or a distribution of LET can be determined. The predicted distribution of dose and/or a distribution of LET can comprise a value of the corresponding quantities for each of the voxels. The treatment plan can comprise delivery of more than one beam. This is done for several reasons: to produce a distribution of dose uniform and conformed to the tumor, to distribute the dose to healthy tissue on different entries (e.g., so that each entry carries a lower dose but all of them converge in the tumor), or to decrease the uncertainties. Using the techniques described herein, a distribution of LET coming from each beam can be calculated. A distribution of LET for the whole plan can also be calculated (e.g., based on the distribution for each beam). The treatment plan can comprise one or more treatment parameters. The treatment parameters can be determined, adjusted, updated, modified, optimized, and/or the like based on a determined dose, LET, energy imparted to a domain, any other value calculated using the techniques disclosed herein, and/or the like. The treatment parameters can comprise a number of beams to be used, angles of incidence, energy and field size for each one of the beams, relative weight (which is, roughly, the number of particles coming from that beam) of the beam, and/or the like.

The results of the techniques disclosed herein can comprise a determination of values for each of a plurality of sites/domains. A voxel (e.g., normally, much larger than a site) can be considered as completely filled by a regular grid of sites/domains. The number of protons in the voxel can be determined. The number of events produced by those protons in all the sites/domains contained in the voxel can be determined. The results can be divided by the number of sites in the voxel.

Additional details are described using the follow detailed explanation and examples. The concept of electronic stopping power—or unrestricted LET—could be considered to measure the energy deposited by particle beams due to electronic collisions in cellular or sub-cellular regions. However, there are at least two relevant considerations disregarded by this quantity: the energy transported out of these regions by secondary electrons and the finite range of protons[11]; in other words, situations of fast changes of LET in short paths, which occurs in the trajectory end of the beam. The first can be incorporated in the concept of restricted linear energy transfer[8] $L_\Delta$, where the energy deposition by secondary electrons with kinetic energy beyond a cut-off value $\Delta$ is disregarded. Efforts have been devoted to calculate either unrestricted or restricted LET for clinical particle beams in acceptable times in clinical routine. Some analytical approaches have been proposed based on the proton stopping power values[12-15], while other works try to include the effect of the energy carried away by secondary electrons using geometrical considerations to obtain spatially or radially restricted LET[16-18]. However, how to deal with situations in which LET may change significantly across microdosimetric structures remains unclear. This is especially important since in such situations the highest values of LET are produced.

In this disclosure, calculation method of LET based on microdosimetry is proposed to address simultaneously the limitations referred above, e.g., both situations in which restricted LET applies and when LET varies along microscopic structures. The resulting distributions from these simulations were used in this work as input data to generate analytical models to calculate LET, and the following sections describe these models in detail. The use of these models to calculate microdosimetry-based LET in clinical particle beams may be the only accurate approach available in clinically reasonable times, since full Monte Carlo microdosimetric LET calculations would need to descend to the track-structure level of detail, which is unaffordable in terms of computation.

Example methods and materials in accordance with the present disclosure are described as follows.

Definitions of relevant LET and microdosimetry concepts are described as follows.

Linear energy transfer (LET) is a non-stochastic quantity that considers the mean energy lost by a charged particle per unit path length. When dealing with a field of charged particles with diverse energies, as in the case of a clinical beam, a different value of LET can be found for each particle. Therefore, rather than a single LET value, a spatial distribution of LET has to be considered in a patient. Thus, it is convenient to reduce that distribution to average values, which can be done in two different ways: one is the fluence-based average, traditionally called track-averaged LET, $\bar{L}_T$; while in the second one, is called dose-averaged LET, $\bar{L}_D$, where the LET of each particle is weighted by its contribution to the local dose[12]. When energy imparted into a certain region is considered instead of the energy lost by the particle, the concept of energy-restricted LET, $L_\Delta$, becomes useful.

In microdosimetry, a site is a region of the irradiated volume with a given shape and microscopic dimension[19]. Although any shape can be considered, this work is restricted to spherical sites for simplicity. When a charged particle strikes a site, a stochastic amount of energy, $\varepsilon$, is imparted to it, carried by both the particle itself and the secondary electrons generated in electronic collisions. The term "imparted" means that energy is considered to be deposited locally, i.e., within the site. Each energy deposition resulting from a different primary particle and its showers of secondary particles is called an event. In calculating $\bar{L}_D$, only electrons may be taken into consideration as secondary particles in each event; this implies that other types of secondary particles (e.g. alphas) must then be considered as separate contributors to $\bar{L}_D$. Therefore, when a number of particles impact on a site, a distribution of energy imparted per event, so-called single-event distribution[20], is originated, with average energy imparted $\bar{\varepsilon}$ and variance $\sigma_\varepsilon^2$.

The techniques described herein relates to a clinical particle beam irradiating a biological target. Tissues can be modeled as composed of sites, also called domains[21], which may represent cells or sub-cellular critical structures. The distributions of energy imparted in sites by a beam of particle can be calculated with a given energetic spectrum. This beam is considered to be broad enough to laterally cover all the site plus a certain margin used to ensure that all energy transfers imparted by secondary electrons generated outside the domain are accounted for.

In this case, for any proton randomly selected from the incidental beam, the portion of its track inside the site is also a stochastic quantity. Protons are assumed to travel in a straight line, which is a good approximation as long as non-electronic collisions are disregarded in the analysis[22]. The path of the track the proton travels within the site is called segment length[23] (s). This definition applies to both when protons stop in the site and when they completely traverse it. This quantity is used to define lineal energy ($y_s$) as the quotient between the energy imparted to the site in an event and the mean segment length:

$$y_s = \frac{\varepsilon}{\bar{s}}. \tag{1}$$

The subscript s indicates that segment length is used to define lineal energy. This definition of lineal energy is different and novel in comparison to conventional approaches. For example, the terms "segment length" and "chord length" can be understood to have different meanings. The segment length can be the actual segment of the particle track in the site in all cases (e.g., including the cases in which the particle stops in the site, called "stoppers"). Chord length can refer to the geometrical problem of calculating the distribution of intersections between a (infinite) straight line and the site (a sphere, in our case). Chord length only takes into consideration particles that completely traverse a domain or site (called "crossers"). The traditional definition of lineal energy uses chord length instead of segment length, which means that its applicability was restricted only to "crossers". By using segment length, the present techniques extending that definition to include "stoppers".

Lineal energy is, therefore, a stochastic quantity with its own distribution of frequencies, characterized by the frequency probability density $f(y_s)$, whose average is denoted as $\bar{y}_{F,s}$. A related distribution of $y_s$ considers the dose absorbed by the tissue in each event with lineal energy $y_s$. This is called dose distribution of $y_s$, $d(y_s)$, and its average is called dose-mean lineal energy[20], $\bar{y}_{D,s}$. Since lineal energy is proportional to the dose absorbed by the site, the dose distribution of y is essentially a weighted distribution multiplied by a constant factor, i.e., $d(y_s) \propto y_s f(y_s)$. Therefore, the averages are related by the following equation, which applies to all frequency and weighted averages[9]:

$$\bar{y}_{D,s} = \bar{y}_{F,s}\left(1 + \frac{\sigma_{y_s}^2}{\bar{y}_{F,s}^2}\right) = \frac{\bar{\varepsilon}}{\bar{s}}\left(1 + \frac{\sigma_\varepsilon^2}{\bar{\varepsilon}^2}\right), \tag{2}$$

where $\sigma_{y_s}^2$ is the variance of the frequency distribution of $y_s$. The second equality is obtained from the definition of $y_s$ in equation (1).

Segment distribution of LET is described as follows.

According to equation (2), $\bar{y}_{D,s}$ is not only related to the average of the frequency distribution of lineal energy in the site, but it also takes into account the variability of that distribution. It can be shown[9] that three factors are involved in the different values of $y_s$ for each case: the different LET of the protons in the site, the different chord length of each proton and the energy straggling. This can be formulated in terms of the variance of each variability source. By considering equation (2) one can obtain the variance of the distribution of segment length in terms of the average of its weighted distribution $d(s)=sf(s)$, also called weighted-mean segment length, $\bar{s}_D$. Additionally, the variance of the straggling distribution can be expressed as $\delta_2/\varepsilon$, where $\delta_2$ is also the weighted-average of the distribution of energy imparted into the site per collision[24].

Disclosed herein is an extension of the applicability of the LET concept based on the following main idea: the variability of LET in the site can be decomposed into two different terms. In the situation in which protons have no appreciable change of LET in the site, a field of protons striking the site with different LET, or, equivalently, different energy, produce a variety of LET values. Thus, a "field distribution" of LET is produced by different protons. On the other hand, if a single proton loses an appreciable amount of its kinetic energy inside the site, its stopping power and, consequently, its LET are not unique as they can vary considerably in the proton path within the site. This case in which a proton changes its $L_\Delta$ within the site has not been previously considered in the microdosimetry literature, since LET is a macroscopic concept and such a change would have a stochastic nature. In order to overcome the indetermination on the LET concept, a new distribution of LET values can be defined based on this variability within the site. This distribution can be understood as follows. Let $dx$ be an element of length small enough so that $L_\Delta$ can be considered constant along $dx$ for each proton energy. Then, the different values of $L_\Delta$ in each $dx$ of the segment length within the site result in a new LET distribution. This distribution can be called "segment distribution" of LET for each proton traversing the site. This "segment distribution" is also a source of variability in $y_s$, since depending on the actual track segment that intersects the site, the combination of $L_\Delta$ values for the proton in the site might change from event to event. Hence, the total distribution of LET in the considered segment length is produced by the combination of the "field distribution" and the "segment distribution".

Based on the introduction of a new level of variability in the lineal energy due to the segment distribution defined above, the segment-distribution-average value of the dose-weighted distribution of LET is here called "segment-averaged dose-averaged LET", $\bar{L}_{D,s}$. This "segment-average" depends on the shape and size of the site. Again, this quantity is related to the variance of the LET distribution by means of equation (2). Considering all above, from the relation between relative variances of the sources of $y_s$ variability, the following equation for the segment-averaged dose-averaged restricted LET can be obtained by employing analogous arguments to those developed by Kellerer[9]:

$$L_{\Delta,D,s} = \frac{\bar{s}}{\bar{s}_D}\bar{y}_{D,s} - \frac{\delta_2}{\bar{s}_D}. \tag{3}$$

Here, as energy imparted into a spherical site is considered instead of energy lost, the $\Delta$ subscript is added to $\bar{L}_{D,s}$ in equation (3) to indicate dose-averaged restricted LET. Now, $\Delta$ is equal to the energy for secondary electrons that makes their range match the distance they have to travel to escape from the site. Therefore, by employing equation (3), it is possible to obtain a calculation for LET that does not count the energy escaped from each site or biological domain by secondary electrons and the effects of the energy straggling. Additionally, this definition of LET applies to the situation in which the energy imparted per unit length varies appreciably within the site or the extreme situation in which protons stop inside the site.

A particular case of interest: constant LET in the site is described as follows.

When protons completely traverse the site, i.e., when their range is greater than the site diameter, the calculation of the distribution of segment length becomes a purely geometrical problem and it is obtained by determining the intersection between a straight line and the site. This is a well-known and solved problem for a spherical site[25]. In this case, the 'segment length' is called 'chord length' (l). For spherical sites with diameter d, the chord length distribution is given by $f(l)=2l/d^2$ ($0 \le l \le d$), with average $\bar{l}=2d/3$. This quantity is traditionally used in microdosimetry to define lineal energy (y) instead of the more general segment length[20] defined above. Therefore, in this particular case, (1) becomes:

$$y = \frac{\varepsilon}{\bar{l}}. \tag{4}$$

The case in which protons have a kinetic energy large enough to consider that their LET does not change within the site is described as follows. In this case, furthermore, protons always cross the site completely thus $s \to 1$. Also, under constant LET conditions, only the "field distribution" of LET plays a role. Therefore, in this limit, $\bar{L}_{\Delta,D,s} \to \bar{L}_{\Delta,D}$ and equation (3) becomes:

$$L_{\Delta,D} = \frac{\bar{l}}{\bar{l}_D}\bar{y}_D - \frac{\delta_2}{\bar{l}_D} = \frac{8}{9}\bar{y}_D - \frac{4\delta_2}{3d}, \tag{5}$$

where the last equality is valid only for spherical sites with diameter d. Equation (5) is not new[8,9] but now it is presented as a particular case of Equation (3) to determine the dose-averaged LET of particle beams. Therefore, its validity can be extended by presenting a more general theory in equation (3), in which this result is included.

Monte Carlo simulations for monoenergetic protons and its application to poly-energetic (clinical) beams are described as follows.

The segment-averaged LET definition is, generally, inconvenient since it depends on the site shape and dimension and, therefore, produces different values for each site considered. Moreover, segment length for low energy protons are complicated to calculate analytically, thus using equation (3) instead of equation (5) seems to add complexity to LET calculations. However, by using Monte Carlo track structure (MCTS) simulations, all these quantities can be obtained. Furthermore, the problem of calculating $\bar{y}_{D,s}$ and $\bar{L}_{\Delta,D,s}$ in a poly-energetic (clinical) beam can be decomposed into simulations of monoenergetic protons, from which an energy kernel can be developed starting from the corresponding distributions of energy imparted. Then, if the proton clinical beam is composed by an energy spectrum given by $\phi(E)$, as the energy imparted distribution is independent for each monoenergetic proton, the average, $\bar{\varepsilon}_\phi$, and the variance of the total distribution of energy imparted, $\sigma_{\varepsilon_\phi}^2$, (i.e. considering the whole fluence) are given, respectively, by $$\bar{\varepsilon}_\phi = \frac{\int \phi(E)\bar{\varepsilon}(E)dE}{\int \phi(E)dE}, \tag{6}$$

$$\sigma_{\varepsilon_\phi}^2 = \frac{\int \phi(E)\sigma_\varepsilon^2(E)dE}{\int \phi(E)dE}, \tag{7}$$

where $\bar{\varepsilon}(E)$ and $\sigma_\varepsilon^2(E)$ are the average and the variance of the distribution of energy imparted for a proton of energy E, respectively. The average $\bar{s}$ and the variance $\sigma_s^2$ of the distribution of segment length (which includes the case in which chord length is applicable) might be obtained in a similar way from the monoenergetic cases. Therefore, the $\bar{y}_{s,D}$ value for a poly-energetic beam can be calculated from equation (2), in which the values calculated using equations (6-7) have to be inserted for the average and the variance of the distribution of energy imparted.

The last quantity to calculate $\bar{L}_{\Delta,D,s}$ by means of equation (3) is $\delta_2$, as $\bar{s}_D$ can be obtained from $\bar{s}$ and $\sigma_s^2$. This is the weighted average of the distribution of energy imparted per collision in the site. Consequently, it can be expressed as:

$$\delta_2 = \delta_1\left(1 + \frac{\sigma_\delta^2}{\delta_1^2}\right), \tag{8}$$

where $\delta_1$ and $\sigma_\delta^2$ are, respectively, the average and the variance of the frequency distribution of energy imparted per collision. These two latter quantities are additive in the same way that the average and the variance of the distribution of energy imparted per event are. Therefore, both $\delta_1$ and $\sigma_\delta^2$ can be obtained for a poly-energetic beam from monoenergetic data by expressions similar to equations (6-7). In general, $\bar{L}_{\Delta,D,s}$ can be derived for mono-energetic or poly-energetic (clinical) beams using equations (4-5, 8) by collecting monoenergetic data for $\bar{\varepsilon}(E)$, $\sigma_\varepsilon^2(E)$, $\bar{s}(E)$, $\bar{s}_D(E)$, $\delta_1(E)$ and $\sigma_\delta^2(E)$ and then integrating over the different energies involved in the spectral fluence distribution of the beam. Additionally, specific energy is defined as $z=\varepsilon/m$ where m is the mass of the site- and its average is the absorbed dose in the site, D. Therefore, by using equation (6) is possible to calculate the absorbed dose for the given beam as $D=\bar{z}=\bar{\varepsilon}_\phi/m$.

Figure 3:
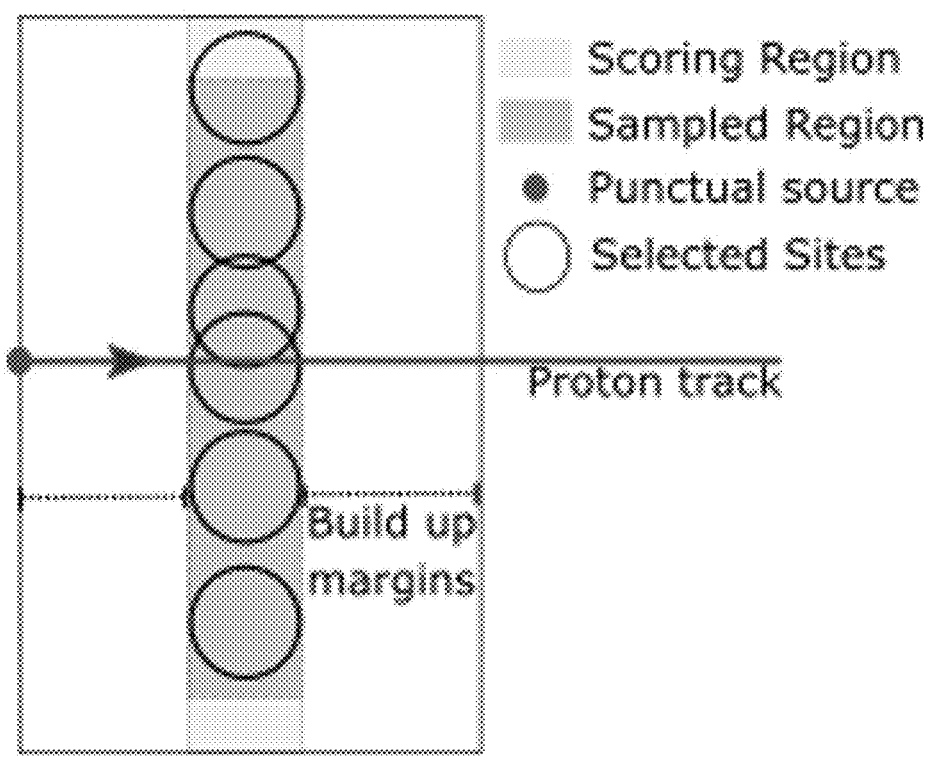
FIG. 3 shows a setup for simulations carried out in Geant4-DNA.

For the reasons indicated in the paragraph above, monoenergetic protons and their secondary electron tracks were simulated in water using Geant4-DNA[26-29]. While the description below and elsewhere herein may reference protons, it should be understood that the same techniques may be applied to other particles used in a therapy beam. Three different site diameters were used to sample microdosimetric energy distributions: 1 μm, 5 μm and 10 μm. Proton tracks originated from a point source were arranged to penetrate a water-made box and the position of the spherical site was uniformly sampled in a slab of thickness equal to its diameter, which is indeed the length of the track segment analyzed (FIG. 3). A margin equal to the maximum range of the secondary electrons generated by protons was added both upstream and downstream the scoring region, where the site is randomly placed, in order to assure charged particle equilibrium condition in the site. This approach is geometrically equivalent to the situation in which the site is fixed in space and a broad beam traverses it. Geant4-DNA allows the tracking of electrons down to ~10 eV, in which case the energy is considered to be deposited locally. Although protons with energy down to 10 keV have been simulated, calculations below 100 keV were only taken into account to obtain the distribution of segment length, and not for the distribution of energy imparted. This is because most of the secondary electrons generated by protons of such low energies have energies below the lower limit of Geant4-DNA, mentioned above. However, these simulations are still valid for obtaining the distribution of segment length. Furthermore, simulations were performed for proton energies up to 100 MeV, which is the upper limit for Geant4-DNA to track protons. To obtain the distribution of energy imparted per collision, and its sole contribution to the variance of energy imparted, the site position can be fixed in a way that the proton path intersected it exactly defining a length equal to the mean segment length. Simulations were performed by using our computing cluster hosted at CICA (Seville, Spain), consisting of 24 computational nodes with 2×12C AMD Abu Dhabi 6344 (2.6 GHz/16 MB L3).

FIG. 3 shows a setup for simulations carried out in Geant4-DNA. Monoenergetic protons emerge from a point source, travelling through a water box. The region in which the site can be sampled (in gray color) is one site diameter in-width and it is laterally extended to ensure any secondary electron generated by the proton stops in the box and its energy can be accounted. Margins upstream and downstream are added to provide electronic equilibrium conditions in the scoring region. Some possible site positions are shown in the diagram.

An example model for the average and variance of the distribution of energy imparted for monoenergetic proton beams is described as follows.

Analytical functions to model the behavior of the average and the variance—or, equivalently, the standard deviation—of the distribution of energy imparted by protons of different energies are presented in this section. A phenomenological function of the proton incidental energy for the average energy imparted ($\bar{\varepsilon}(E)$) can be defined as follows: it is expected that the energy imparted is proportional to the stopping power of the proton at that energy. According to the Bethe formula[30] in its non-relativistic approximation, this dependency is proportional to $\log(a \cdot E)/E$, where $a=4m_e/m_p I=27.9$ MeV$^{-1}$, being $m_e$ and $m_p$ the electron and proton mass at rest, respectively, and I is the ionization potential in water: 78 eV[31]. However, this dependency has a saturated behavior due to the finite dimension of the site, e.g., due to the nature of a restricted LET. When the incidental proton has a very low energy, all the secondary electrons deposit their energy locally within the site and the amount of energy imparted increases as the proton energy does. However, as energy further increases, some secondary electrons can leave the site so that the energy imparted to the site per collision does not increase anymore. This can be modeled by using an error function. Thus, proposed is $\bar{\varepsilon}(E) \propto \text{erf}(kE^q) \cdot \log(27.9 \, E)/E \cdot R/(R+2d/3)$, where k and q were introduced as two degrees of freedom to fit the error function to the Geant4-DNA calculations. Furthermore, when proton range is considerably shorter than the site dimension, the probability for a proton track located laterally far from the site center to enter the site starts to decrease due to the sphere curvature. Therefore, $\bar{\varepsilon}(E)$ should also be proportional to this probability of interaction, since the greater the probability, the greater the number of collisions in the site. According to the model by Santa Cruz et al.[32] for event statistics, the combined probability for producing an event for protons that stop in the site and protons that traverse completely the site is given by R/(R+2d/3), where R is the range of the proton and d is the diameter of the site. The relation between the range and the energy can be taken from the Bragg-Kleeman rule[33], from which R(E)=αE[p]. Taking data from NIST database[34] for the CSDA range of protons, the phenomenological function can be fitted to the $\bar{\varepsilon}(E)$ data obtained from the MC calculations, from which can be obtained the values a=19.53 μm/MeV[p] and p=1.799. From all the above, the following function can be proposed to model the average energy imparted per single event:

$$\bar{\varepsilon}(E) = C_\varepsilon \cdot \mathrm{erf}(k_\varepsilon E^{q_\varepsilon}) \cdot \log(27.9\ E + b_\varepsilon) \cdot \frac{19.53 \cdot E^{(1.799-1)} + e_\varepsilon}{19.53 \cdot E^{1.799} + 2d/3}, \quad (9)$$

where $C_\varepsilon$ is a proportionality constant, and $b_\varepsilon$ and $e_\varepsilon$ are parameters, non-physically meaningful, introduced to avoid the indetermination at E=0 and to take into account the fact that segment-averaged energies are being obtained, and not strictly the energy imparted by protons of a unique energy.

As the distribution of energy imparted follows a compound Poisson process[9], it is expected that its standard deviation follows a similar behavior to its average. However, as the site diameter becomes larger, an additional effect takes place, which can be observed in FIG. 4B: a spike emerges in the low energy part of the curve for the standard deviation. To include this effect in the model, a Gaussian term G(E) can be subtracted from the expression in equation (9), centered at the energy $E_c$ in which the characteristic basin is observed in those curves. Therefore, the proposed function becomes now:

$$\sigma_\varepsilon(E) = C_\sigma \cdot \mathrm{erf}(k_\sigma E^{q_\sigma}) \cdot \log(27.9 E + b_\sigma) \cdot \frac{19.53 \cdot E^{(1.799-1)} + e_\sigma}{19.53 \cdot E^{1.799} + 2d/3} - C_G \exp(-k_G(E - E_c)), \quad (10)$$

where the Gaussian term is expressed as $G(E) = C_G \exp(-k_G(E-E_c))$ and incorporates three new parameters: $C_G$, $E_c$ and $k_G$.

An example model for the average and weighted-average segment length is described as follows.

For both averages of segment length, the expected behavior is a saturated function, since once the proton has a residual range larger than the site diameter, segment length tends to the chord length and the averages of those distributions are independent on the proton energy or range. A good fit for this particular behavior is:

$$\bar{s}(E) = \frac{2d}{3}(1 - \exp(-k_{sF1}\exp(-k_{sF2}E)), \quad (11)$$

where $k_{sF1}$ and $k_{sF2}$ are two empirical parameters and 2d/3 is the saturation value. The same function is proposed to fit $\bar{s}_D(E)$ to the data to obtain the corresponding parameters $k_{sD1}$ and $k_{sD2}$, but using the weighted-average of the chord length distribution, 3d/4, instead of 2d/3 as saturation value:

$$\bar{s}_D(E) = \frac{3d}{4}(1 - \exp(-k_{sD1}\exp(-k_{sD2}E)), \quad (12)$$

An example model for the straggling functions is described as follows.

Finally, other analytical models can be proposed for the average and the variance—or the standard deviation—of the distribution of energy imparted per collision. As argued previously, the average energy imparted per collision should increase with the proton energy at very low energies until reaching a maximum point in which the amount of energy transported out of the site by the secondary electrons compensates the increase of energy imparted due to the proton kinetic energy increase. Beyond that point, the function slowly decreases due to the fact that the energy escape component becomes more important than the kinetic energy increase. A function that models well this is given by:

$$\delta_1(E) = C_{\delta_1}(1 - \exp(k_{\delta_1,1} \cdot E))\exp(-k_{\delta_1,2} \cdot E^{p_{\delta_1}}), \quad (13)$$

where $C_{\delta_1}$, $k_{\delta_1,1}$, $k_{\delta_1,2}$ and $p_{\delta_1}$ are the fitting parameters. Following the same reasoning than for the standard deviation of the imparted energy, $\sigma_\delta(E)$ can be modeled by fitting the same functional form than in equation (12) to the calculated MC data to obtain the corresponding four parameters $C_{\sigma_\delta}$, $k_{\sigma_\delta,1}$, $k_{\sigma_\delta,2}$ and $p_{\sigma_\delta}$.

All the fitting to the Monte Carlo data was done with the Trust-Region algorithm for the method of non-linear least squares implemented in MATLAB R2018a Curve Fitting toolbox[35].

Example validation for other site dimensions is described as follows

Equations (9) through (12) were produced from MC simulations for site diameters of 1 μm, 5 μm and 10 μm. In order to validate the disclosed approach, additional MC simulations were performed for site diameters of 3 μm and 7 μm and compared to the prediction provided by equations (9-12) for these site dimension.

Figure 4A:
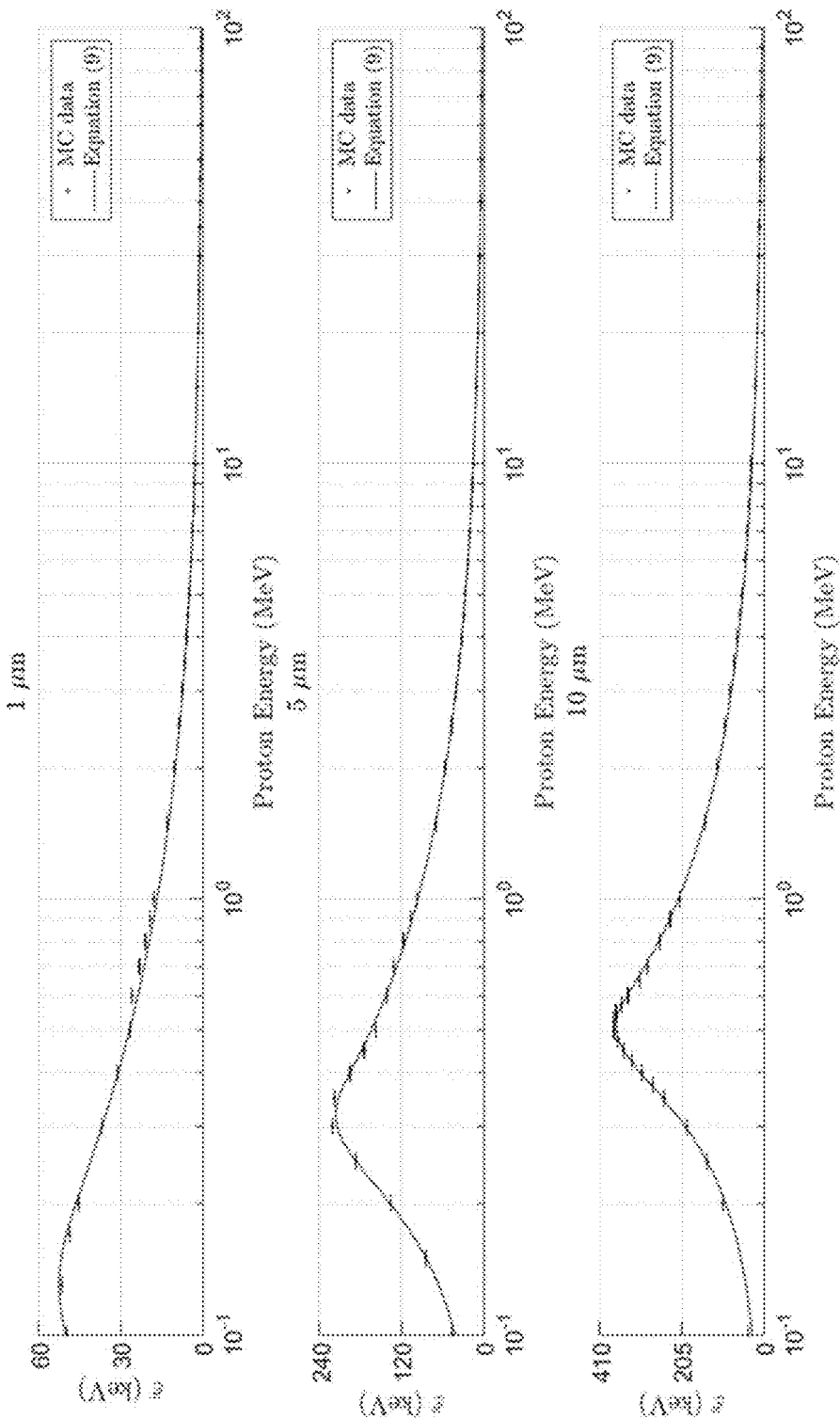
FIG. 4A shows graphs of calculations from MC simulations and corresponding fitted function for average single-event energy imparted to sites with diameters of 1 μm, 5 μm, and 10 μm.
Figure 4B:
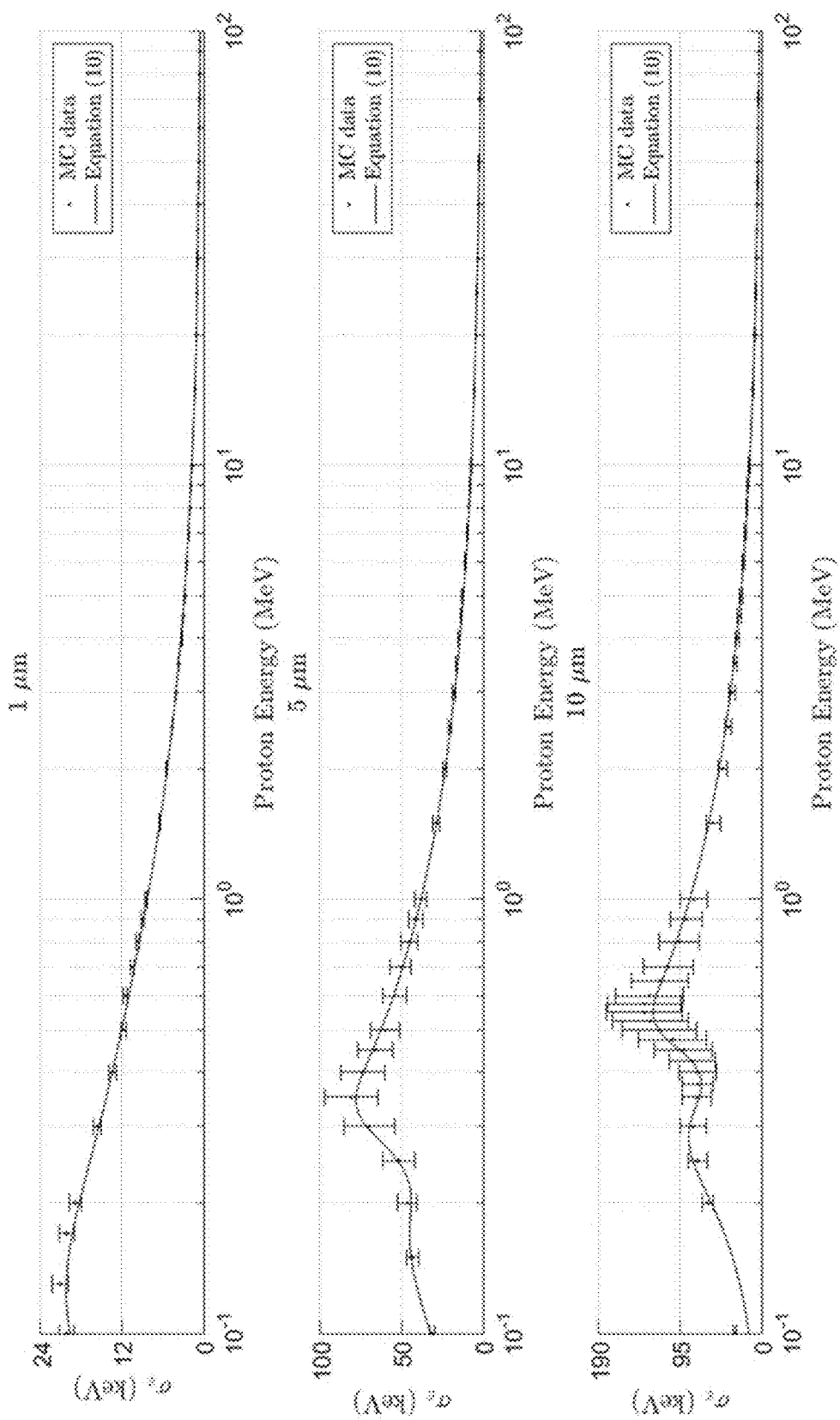
FIG. 4B shows graphs of calculations from MC simulations and corresponding fitted function for the standard deviation of the corresponding distributions of energy imparted to sites with diameters of 1 μm, 5 μm, and 10 μm.

Results of the example methods and techniques above are described as follows. FIGS. 4A-B shows the results of the fitted functions in equations (9-10) for the average and the standard deviation of the single-event energy imparted for protons from 0.1 MeV to 100 MeV irradiating spherical sites with diameter of 1 μm, 5 μm and 10 μm, respectively. Residuals for these fits can be found in FIGS. 11A-B. These figures show data obtained from the MC simulations done with Geant4-DNA in liquid water for monoenergetic protons from 0.1 to 100 MeV (points) and fitted functions, equations (9-10) (lines), for spherical sites with diameter of 1 μm, 5 μm and 10 μm, respectively. FIG. 4A shows graphs for average single-event energy imparted to the site. FIG. 4B shows graphs for the standard deviation of the corresponding distributions of energy imparted. Statistical uncertainties of the MC simulations (1σ) are shown with error bars.

Figure 5:
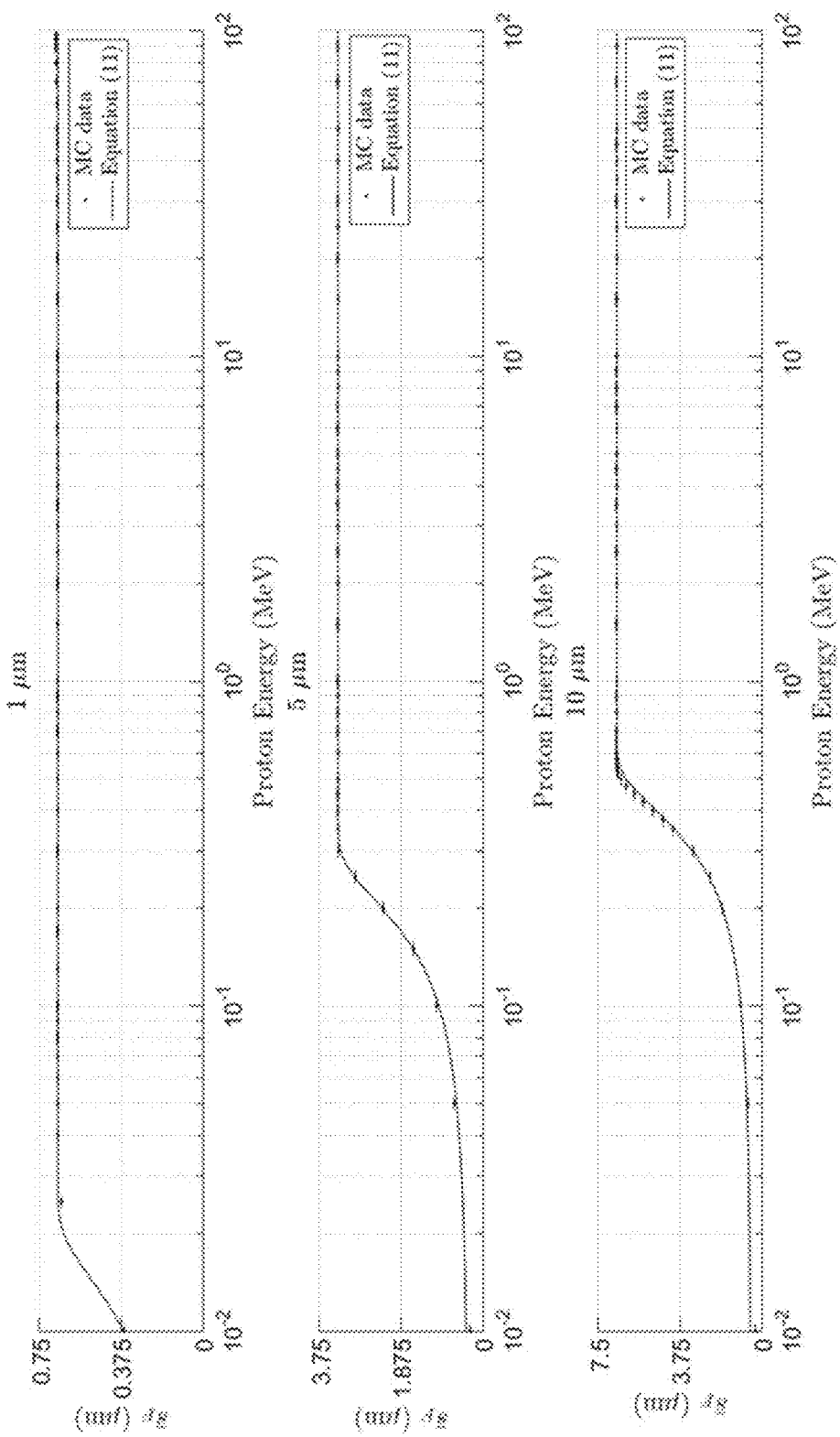
FIG. 5 shows graphs of calculations from MC simulations and corresponding fitted function for average segment length in spherical sites with diameters of 1 μm, 5 μm, and 10 μm.
Figure 12A:
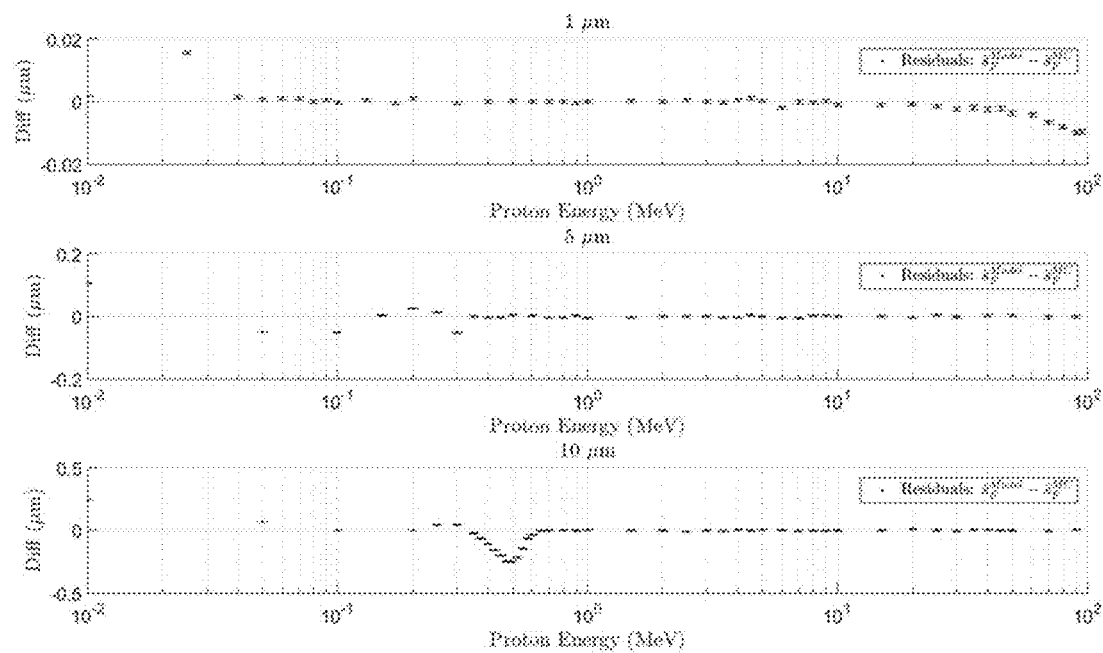
FIG. 12A shows residuals between MC-based and model-based calculations of the average segment length for spherical sites with diameters of 1 μm, 5 μm and 10 μm, respectively.

As for the frequency-average segment length described by protons along the site, the fit of the function proposed in equation (11) to the MC calculations is showed in FIG. 5. In this case, simulations of proton with energies down to 10 keV can be considered, as the energy at which a proton becomes a "stopper" is below 100 keV for spherical sites of 1 μm diameter. Residuals for this fit are shown in FIG. 12A.

Figure 12B:
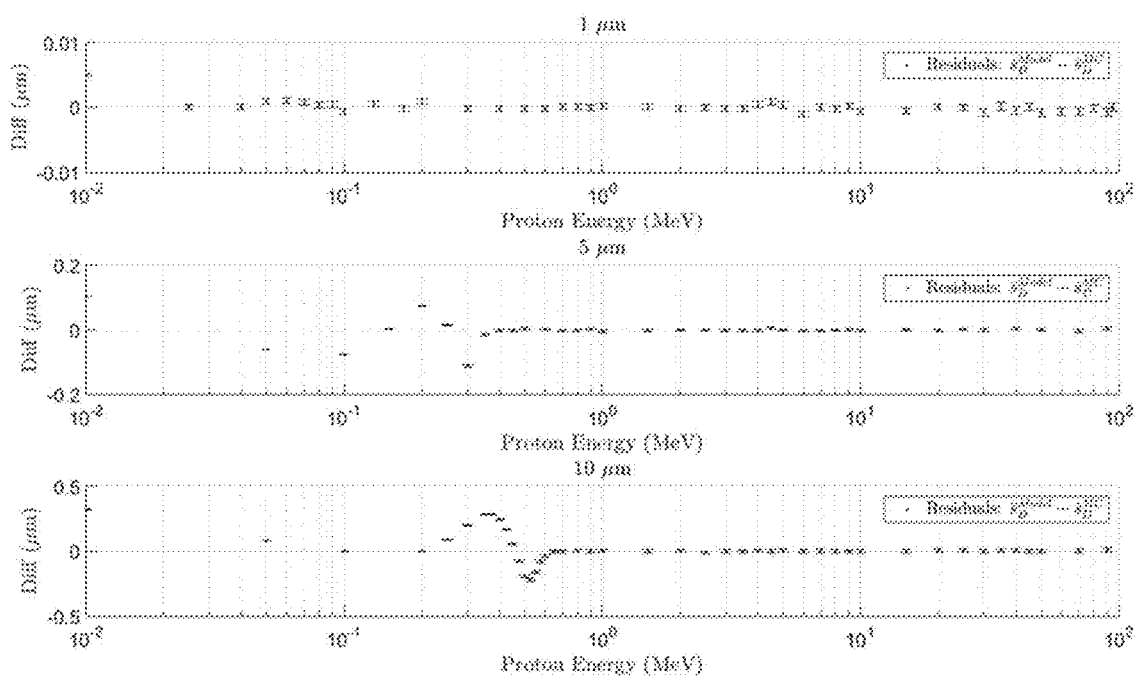
FIG. 12B shows residuals between MC-based and model-based calculations of the weighted-average segment length for spherical sites with diameters of 1 μm, 5 μm and 10 μm, respectively
Figure 13:
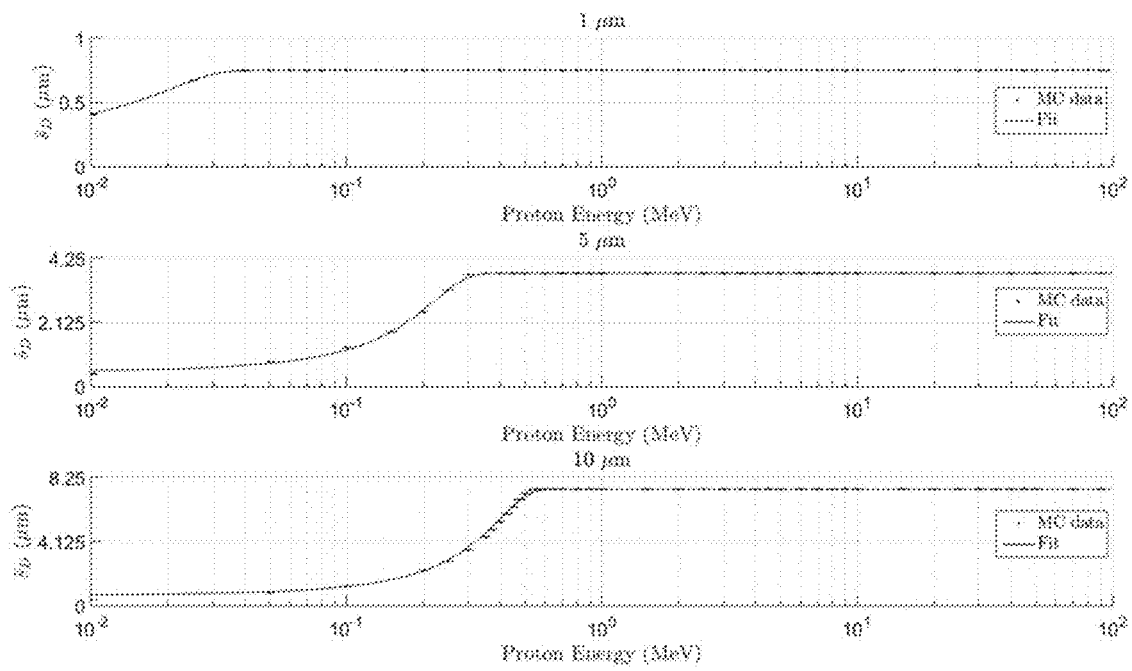
FIG. 13 shows calculations from MC simulations done with Geant4-DNA in liquid water for monoenergetic protons from 0.01 to 100 MeV (points) and corresponding fitted function, equation (12) (lines) for the weighted-average segment length described in spherical sites with diameters of 1 μm, 5 μm and 10 μm, respectively

Results and residuals for weighted average segment length, $\bar{s}_D$, equation (12), are also shown in FIG. 13 and FIG. 12B, respectively.

FIG. 5 shows graphs of calculations from MC simulations done with Geant4-DNA in liquid water for monoenergetic protons from 0.01 to 100 MeV (points) and corresponding fitted function, equation (11) (lines) for the average segment length described in spherical sites with diameters of 1 μm, 5 μm and 10 μm, respectively. Statistical uncertainties of the MC simulation (1σ) are shown with error bars.

Figure 6:
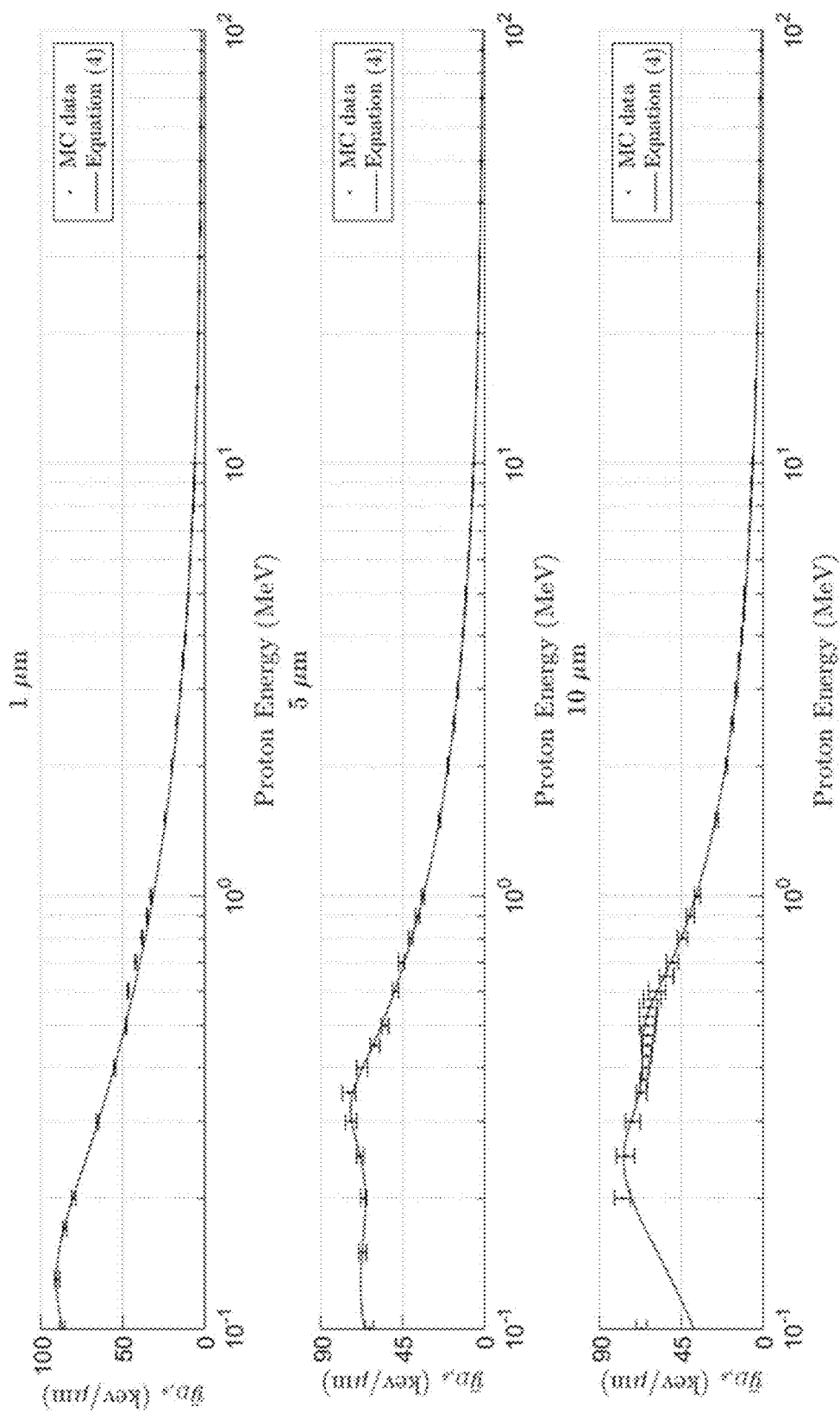
FIG. 6 shows graphs of dose-mean lineal energy obtained from MC simulations and with proposed analytical models (lines) for spherical sites with diameters of 1 μm, 5 μm, and 10 μm.
Figure 14:
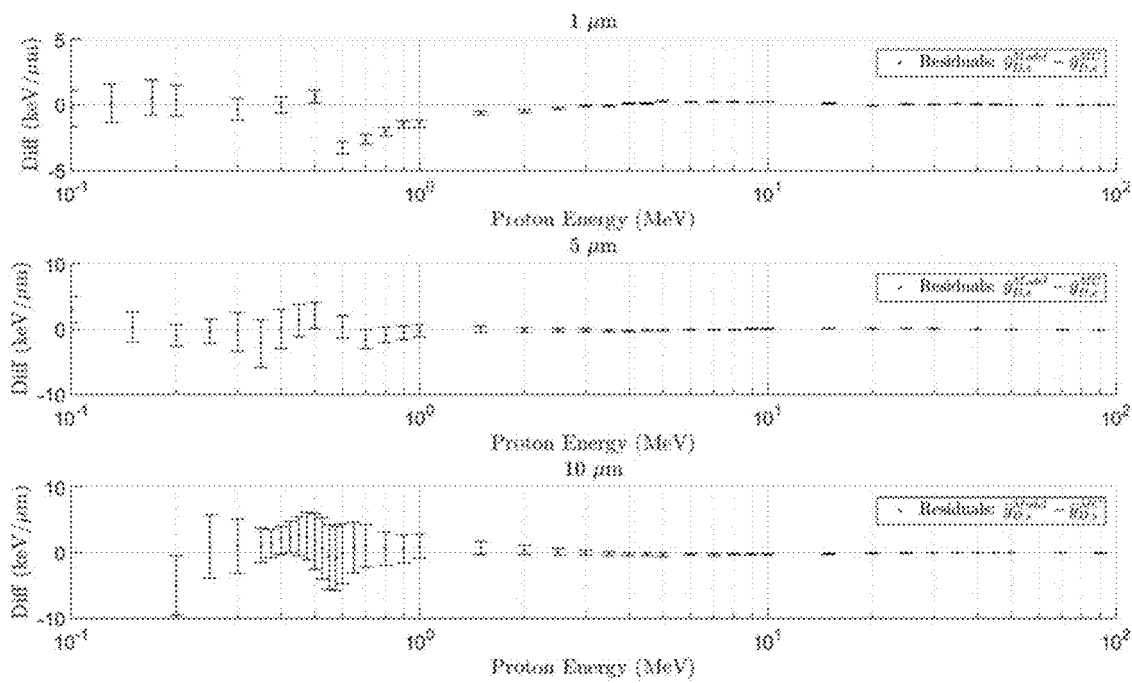
FIG. 14 shows residuals between the dose-mean lineal energy obtained from MC simulations of monoenergetic protons in liquid water done with Geant4-DNA and with our proposed analytical models by using equation (2), for spherical sites with diameters of 1 μm, 5 μm and 10 μm, respectively

Once obtained the previous results, it is possible to calculate $\bar{y}_D$ according to the way specified in equation (2). FIG. 6 shows the comparison between the calculated $\bar{y}_D$ values following this equation by using the calculations from MC simulations and the analytical fitted functions already shown. Differences between calculated values through the MC calculations and the analytical model are shown in FIG. 14.

FIG. 6 shows graphs of dose-mean lineal energy obtained from MC simulations of monoenergetic protons in liquid water done with Geant4-DNA (points), and with the proposed analytical models (lines) by using equation (2), for spherical sites with diameters of 1 μm, 5 μm and 10 μm, respectively. Statistical uncertainties propagated from the MC simulations (1σ) are shown with error bars.

Figure 7:
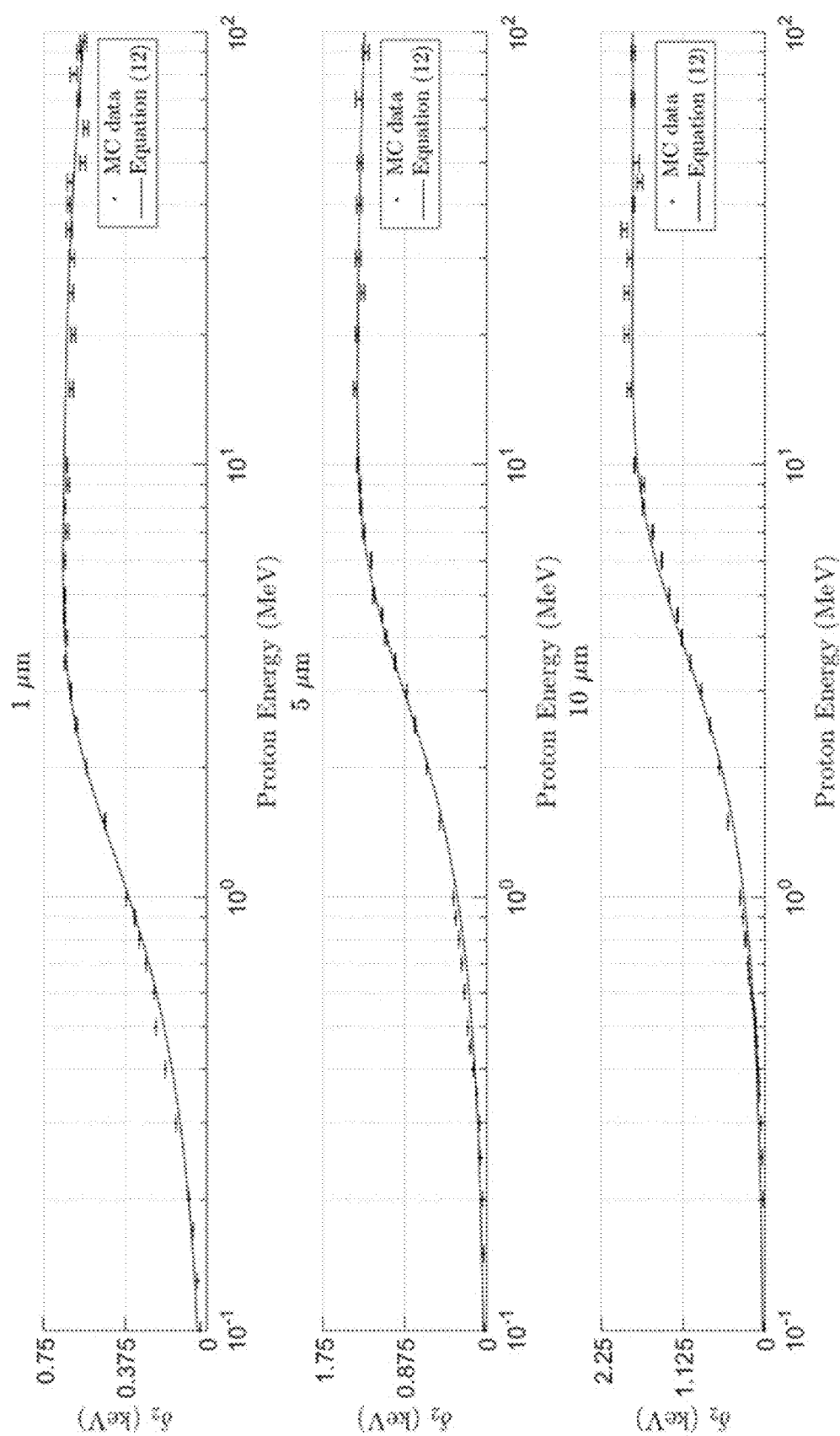
FIG. 7 shows graphs comparing the analytical expression shown in equation (13) and the MC data resulting from Geant4-DNA simulations for the average and the standard deviation of the distribution of imparted energy per collision.

FIG. 7 shows graphs comparing the analytical expression shown in equation (13) and the MC data resulting from Geant4-DNA simulations for the average and the standard deviation of the distribution of imparted energy per collision, $\delta_2(E)$. Results and residuals for the fits for each one of these two functions are shown in FIGS. 15A-B and FIGS. 16A-B respectively. Differences between $\delta_2(E)$ values for MC and analytical calculations are shown in FIG. 17.

Figure 8A:
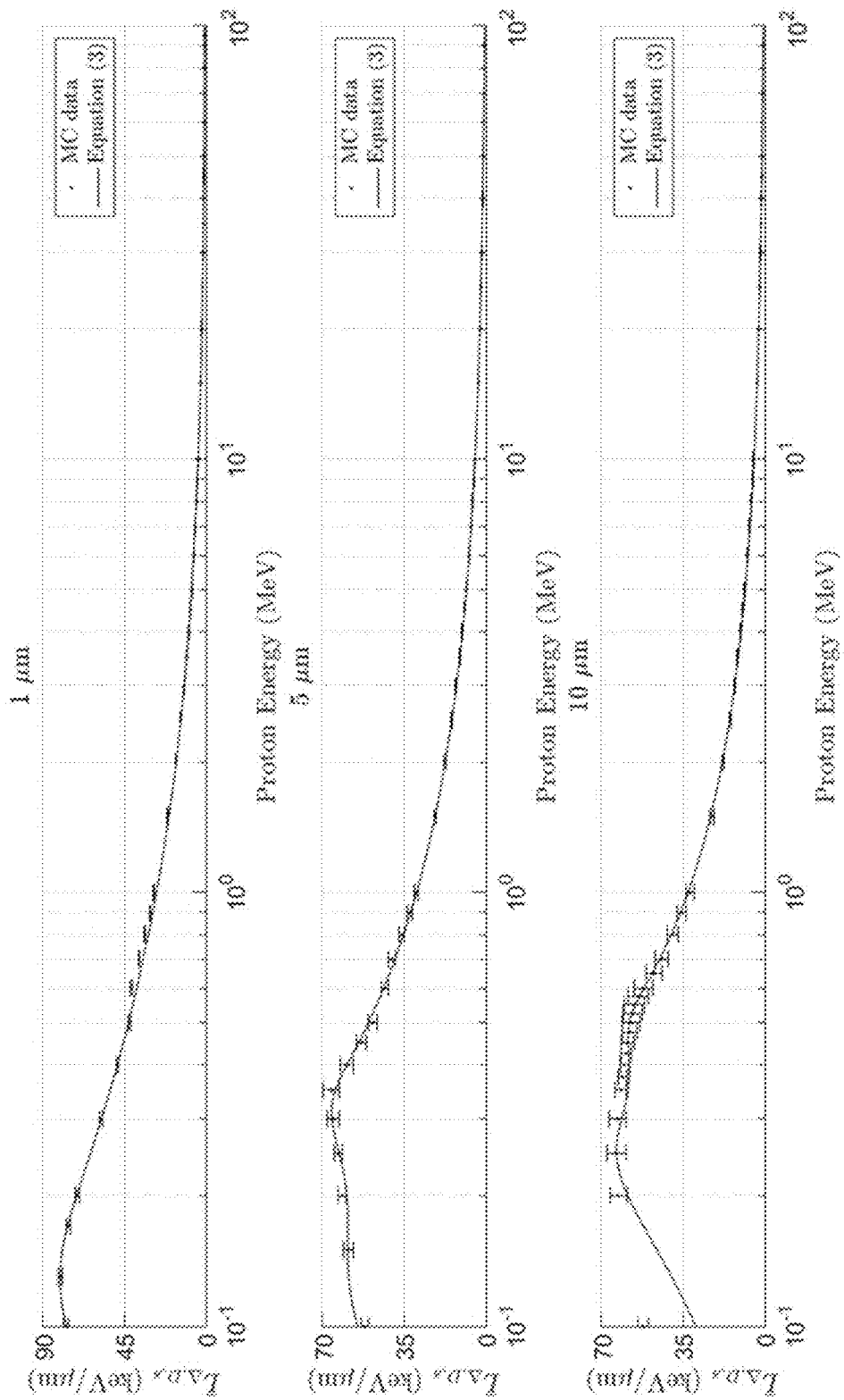
FIG. 8A show shows graphs of segment-averaged dose-averaged restricted LET for spherical site with diameters of 1 μm, 5 μm, and 10 μm.
Figure 8B:
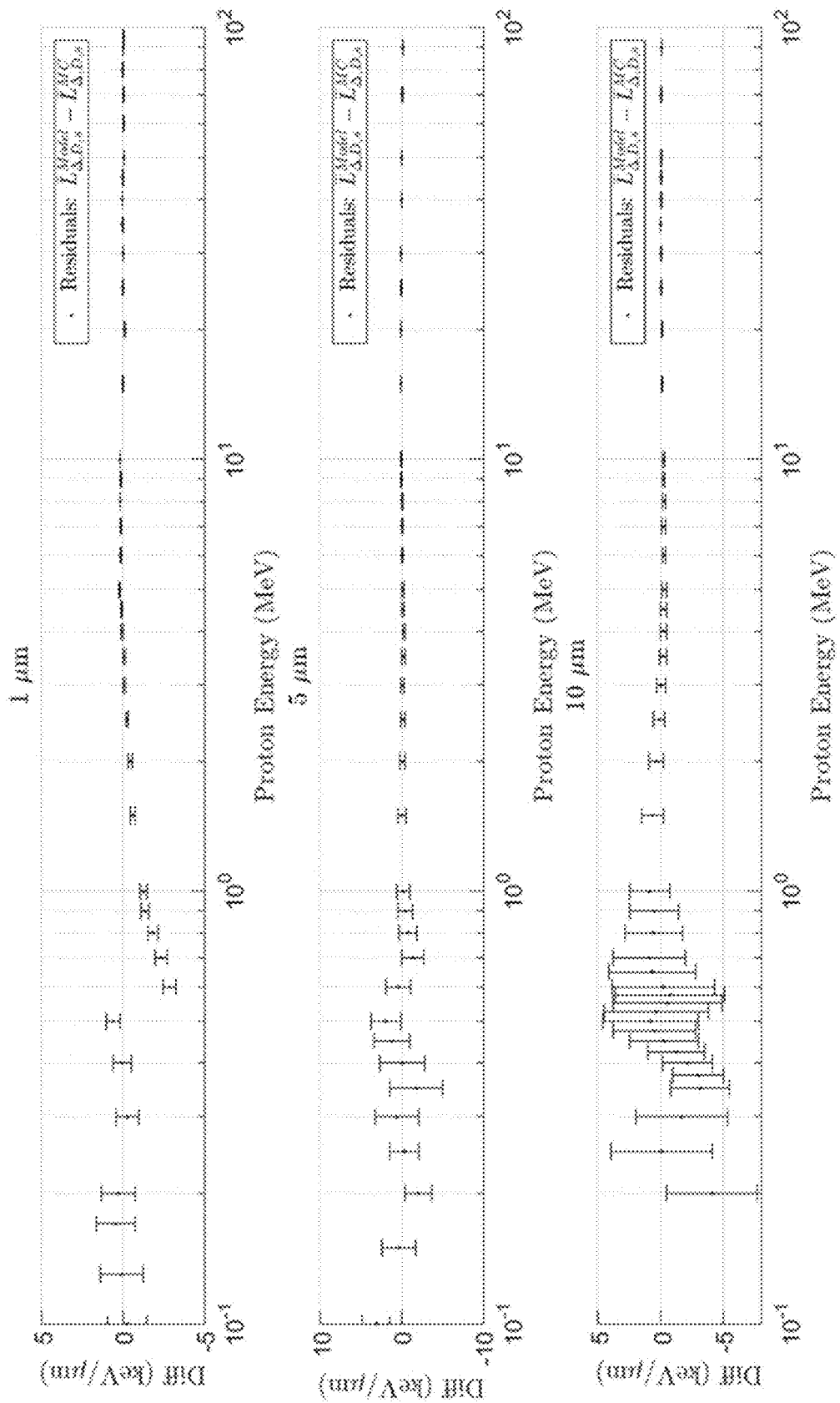
FIG. 8B shows absolute differences between segment-averaged dose-averaged restricted LET calculated with the proposed analytical models and with Geant4-DNA MC simulations.

FIGS. 8A-B shows graphs illustrating weighted average of the distribution of energy imparted per collision, $\delta_2$, calculated for monoenergetic protons in liquid water from Geant4-DNA MC simulations (points), and from the analytical models described in equation (13) (lines) for spherical sites with diameters of 1 μm, 5 μm and 10 μm, respectively. Statistical uncertainties of the MC simulations (1σ) are shown with error bars.

Combining all the results shown above, for the three site diameters considered, it is possible to calculate the segment-averaged dose-averaged restricted LET, $\bar{L}_{\Delta,D,s}$, for each proton energy by means of equation (3). FIGS. 6A-B shows the comparison between the results for $\bar{L}_{\Delta,D,s}$ employing the data coming from the MC simulations and from all the analytical models proposed in this work. Differences between $\bar{L}_{\Delta,D,s}$ values calculated from MC data and the analytical models are also shown in FIGS. 8A-B.

FIG. 8A show shows graphs of segment-averaged dose-averaged restricted LET, $\bar{L}_{\Delta,D,s}$, calculated with Geant4-DNA MC simulations of protons in liquid water (points) and with the proposed analytical models (lines) by using equation (3), for spherical site with diameters of 1 μm, 5 μm and 10 μm, respectively. Statistical uncertainties propagated from the MC simulations (1σ) are shown with error bars. FIG. 8B shows absolute differences between $L_{\Delta,D,s}$ calculated with the proposed analytical models and with Geant4-DNA MC simulations. The point for the 10 μm site and 0.1 MeV is not shown, being this difference equal to 22.64 keV/μm.

The difference for protons at 0.1 MeV is found to be considerably larger than at any other energy for a site of 10 μm diameter. This is due to the low values for $\bar{s}_F$ and $\bar{s}_D$ at that point, which implies that small variations from the MC results for that quantities produce a large deviation for $\bar{L}_{\Delta,D,s}$. Leaving that point out, average differences (model calculations minus G4-DNA computations) are −0.2±0.7 keV/μm for the 1 μm case, 0.0±0.9 keV/μm for the 5 μm case and −0.3±1.1 keV/μm for the 10 μm case, where the uncertainties indicate the standard deviation of the differences. To look at the relevance of found differences, these values can be expressed as relative to the average standard deviation for the Monte Carlo calculations in each case. The average uncertainties (1σ) for the Monte Carlo calculations, respectively, are 0.3 keV/μm, 0.8 keV/μm and 1.4 keV/μm. Consequently, all the average discrepancies between the model and the MC calculations are below 16.

Figure 9A:
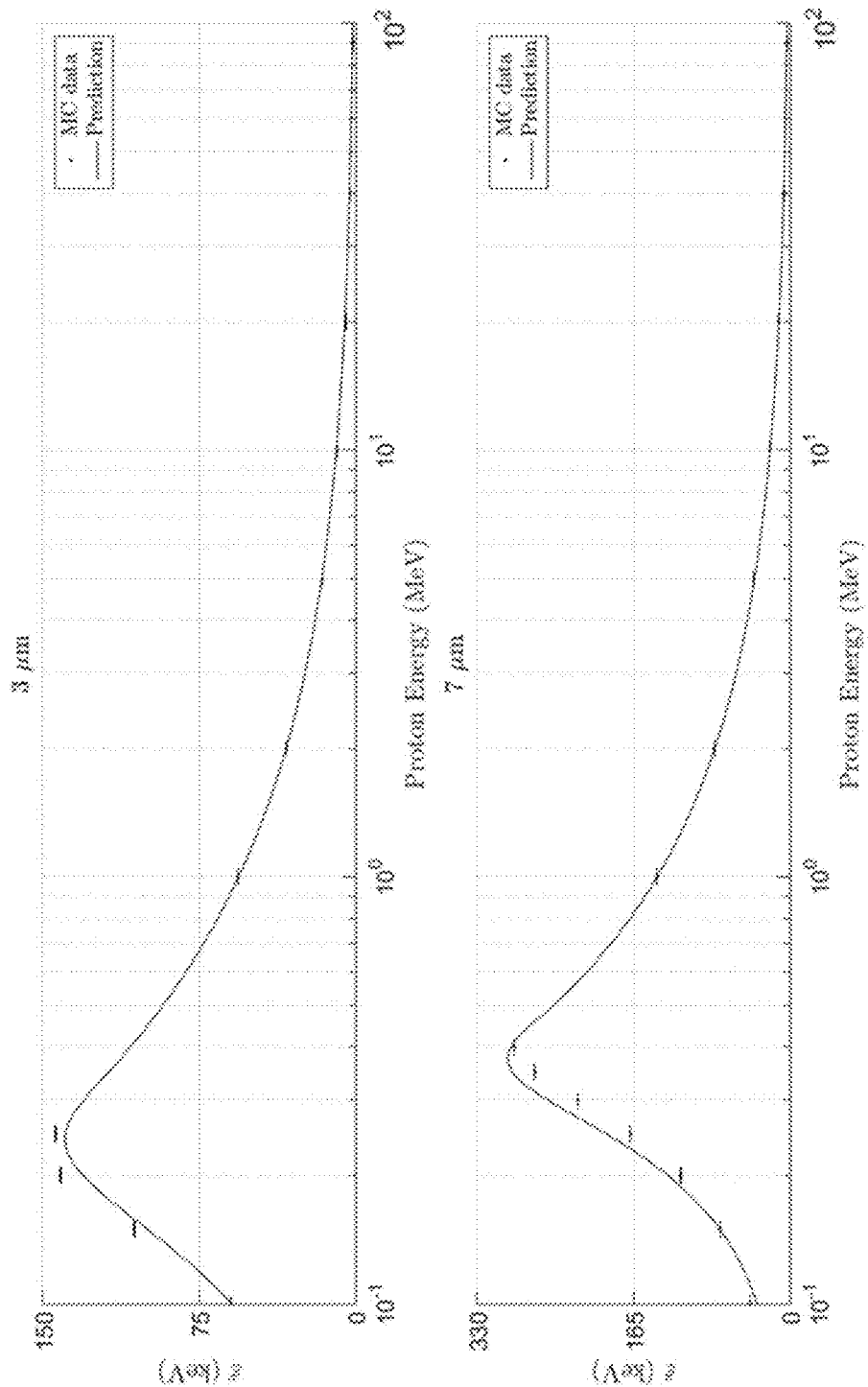
FIG. 9A shows frequency-average of single-event energy imparted to the site for sites of 3 μm and 7 μm, interpolating from the data for sites of 1 μm, 5 μm and 10 μm.
Figure 9B:
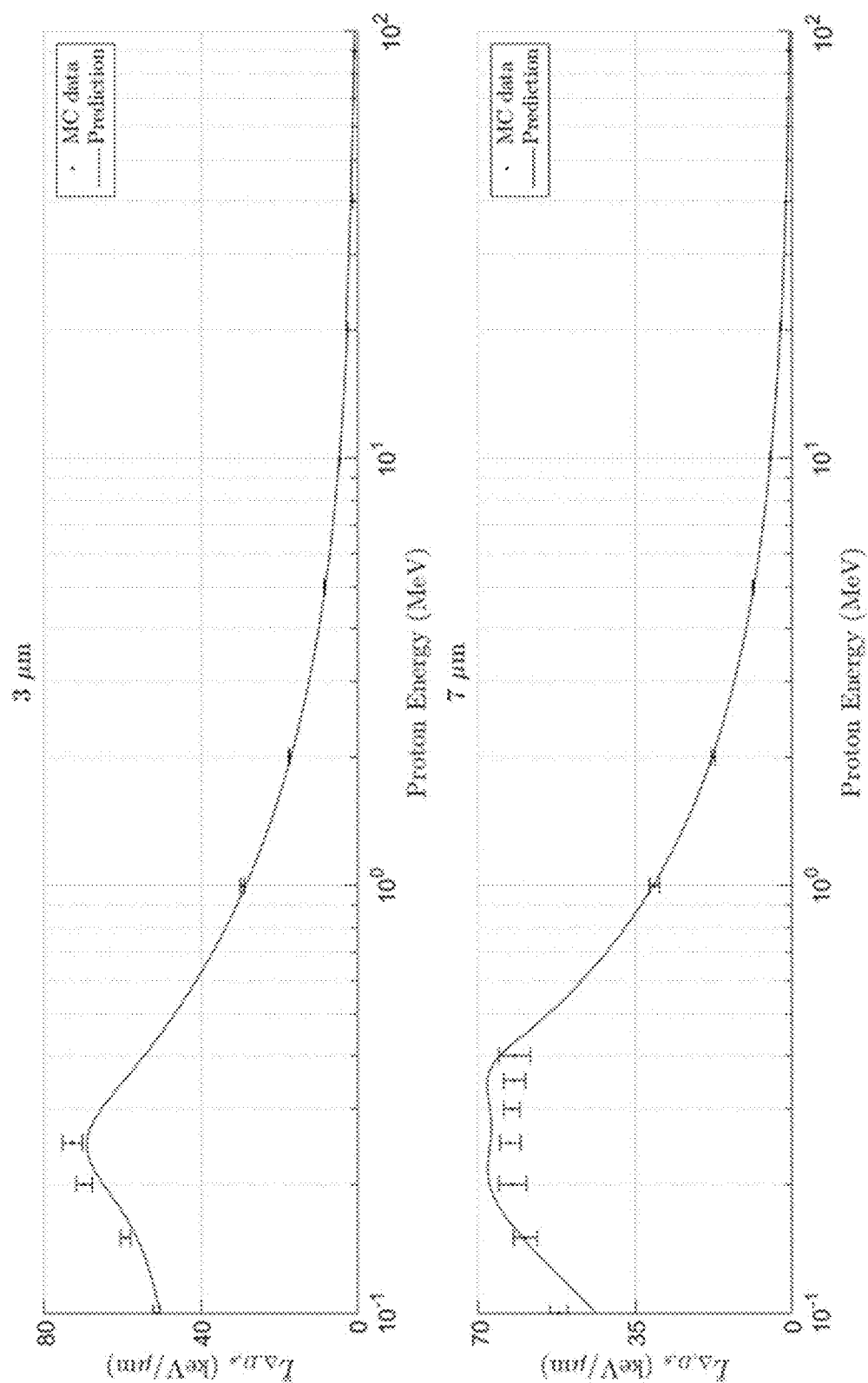
FIG. 9B shows segment-averaged dose-averaged restricted LET for sites of 3 μm and 7 μm, interpolating from the data for sites of 1 μm, 5 μm and 10 μm.
Figure 18A:
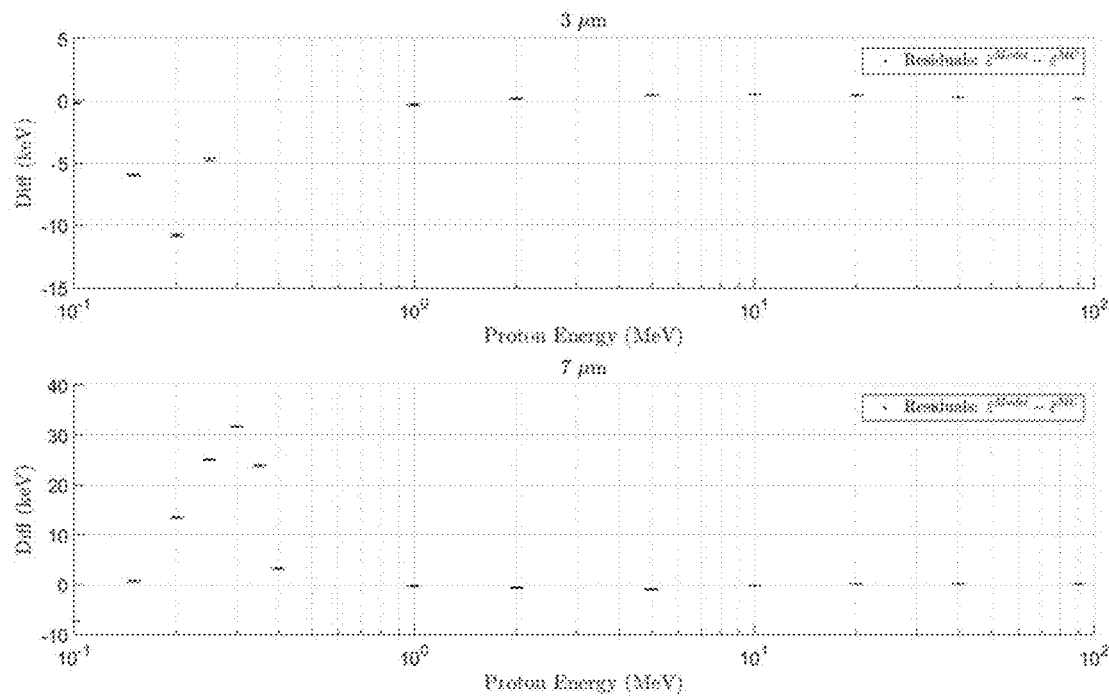
FIG. 18A shows residuals between MC-based and model-based calculations of frequency-average of single-event energy imparted to the site, $\bar{\varepsilon}$, for sites of 3 µm and 7 µm interpolating from data for sites of 1 µm, 5 µm and 10 µm.
Figure 18B:
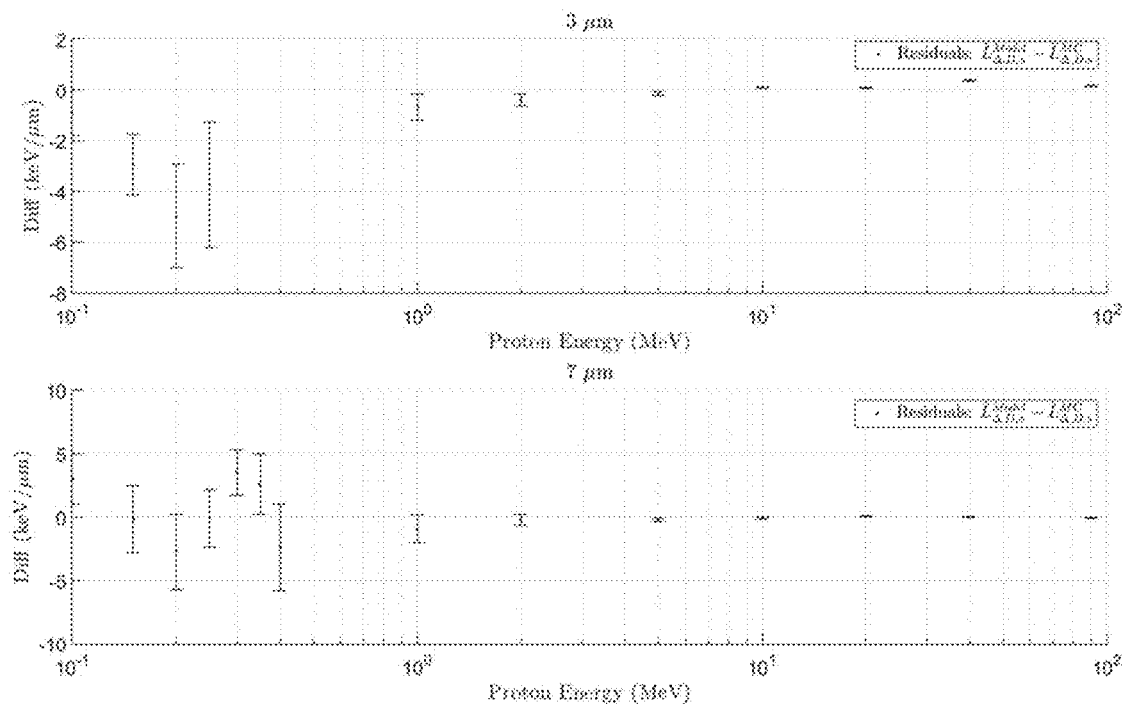
FIG. 18B shows residuals between MC-based and model-based calculations of segment-averaged dose-averaged restricted LET $\bar{L}_{\Delta,D,s}$, for sites of 3 µm and 7 µm interpolating from data for sites of 1 µm, 5 µm and 10 µm. Statistical uncertainties propagated from the MC simulations (1σ) are shown with error bars.

Finally, by interpolating the values of the fitting parameters obtained in the models given by the equations (9-12), a prediction of the average energy imparted and $\bar{L}_{\Delta,D,s}$ for intermediate site diameters can be assessed. FIGS. 9A-B shows predictions for spherical sites with diameters of 3 μm and 7 μm, respectively, compared with the calculations obtained from Geant4-DNA MC simulations. Residuals between the predicted results and the MC data are shown in FIGS. 18A-B.

FIGS. 9A-B show data obtained from the Geant4-DNA MC simulations of monoenergetic protons in liquid water (points) and the prediction resulting from the interpolation of the fitting parameters of the models (lines) for spherical sites with diameter of 3 μm and 7 μm, respectively. FIG. 9A shows frequency-average of single-event energy imparted to the site, $\bar{\epsilon}$; FIG. 9B shows segment-averaged dose-averaged restricted LET $\bar{L}_{\Delta,D,S}$. Statistical uncertainties propagated from the MC simulations (1σ) are shown with error bars.

The average deviation found for the $\bar{L}_{\Delta,D,s}$ prediction with respect to the G4-DNA calculated points is now −1.2±1.8 keV/μm for the 3 μm site and 1.2±3.6 keV/μm for the 7 μm, where the uncertainties refer to the standard deviation of the differences.

Discussion of the results is provided as follows.

Three characteristics make the LET calculation presented in this work different from the collision stopping power: dose-averaging, restriction and segment-averaging. Furthermore, the calculated LET depends on two different parameters: the initial proton kinetic energy and the site dimension. Since spherical sites are used, the latter is characterized by the site diameter. The following discussion analyzes the importance of each characteristic of the disclosed LET calculation depending on the proton energy and the site diameter.

The dose-averaging is incorporated into the calculation by taking into account the standard deviation of the different quantities involved and by using the relative variances relation leading to equation (3). It is, therefore, relevant for all proton energies and site diameters. The restriction is performed by using a given spatial structure to score the energy imparted and, therefore, is implicit in the distributions of single-event energy imparted calculated. This spatial restriction is important in such situations in which secondary electrons generated by the proton from ionizations of molecules of the medium might escape from the site in a non-negligible proportion. This condition is met when either the site is relatively small or the kinetic energy transferred to the electrons is high enough, i.e., the proton energy is high enough to make them escape. Therefore, one can expect to find the main differences between restricted LET and stopping power at higher energies as the site size increases. For the same proton energy, the restricted LET value is higher for larger sites and it tends to converge to the stopping power when an infinitely large site is considered.

On the other hand, the segment-averaging process becomes important in those cases in which the stopping power of the proton changes its value significantly across the site. This happens when either the site is relatively large or the proton energy is low enough. Secondary electrons do not play a role in the latter case because the amount of energy transferred to them is of the order of eV, thus they are not expected to travel long distances from the proton track. It is convenient to notice that the segment-averaging process is similar to integrate the collision stopping power curve S(E) for protons in water along the considered distance, i.e. the site diameter, $$L_{Ds} \approx \int S(E(x)) \frac{dE(x)}{dx} dx / \int \frac{dE(x)}{dx} dx, \quad (13)$$

where E(x) is the energy of the proton at the point x. Therefore, the larger is that distance, the broader and smaller results the new curve's peak with respect to collision stopping power. Additionally, because of the same reason, the new peak will be shifted towards higher energies. This explains why for the 1 μm diameter site such a peak is not observed.

Additionally, the larger the site, the more the stopping power is able to change. This means that a longer portion of the curve of stopping power respect to the proton energy is considered to calculate the segment-average LET. This explains the different positions (on x-axis) and amplitude of the peaks obtained in the curves for the average and the standard deviation of the single-event energy imparted distribution shown in FIGS. 4A-B for different site diameters. As the site becomes larger, the peak gets higher and shifted towards higher initial proton energies because a longer portion of the track is considered, thus a proton is able to stop and deposit all its energy in the site entering with higher initial energies.

The reason for the spike observed in FIG. 4B for $\sigma_\varepsilon$ at large sites (diameter of 5-10 μm) is based on the fact that distributions of energy imparted by protons at very low energies have a tailed shape at the high energy part of the distribution, being this tail due to the events produced by "stoppers". Then, two competitive effects take place when very low energies are considered: as the proton energy increases, (i) the absolute energy imparted grows so that the absolute standard deviation of the distribution does too; but (ii) the number of events produced by "stoppers" decrease (their range become larger), thus the mentioned tail fades away, which makes the standard deviation to decrease. For the 1 μm diameter site, the second effect occurs already below 100 keV, which is why this effect has practically no impact on the curve. However, the larger the site, the higher the energy at which the tail disappears so that, at a certain point, the second effect starts to be noticed, making the standard deviation decrease. Once the tail vanishes, $\sigma_\varepsilon$ follows the dependence of $\bar{\varepsilon}$ with the proton energy.

By means of equation (3), the effects of segment length variability and straggling on the distribution of $y_s$ may be disregarded in the $\bar{L}_{\Delta,D,s}$ value. This is convenient because these two sources of variability for $y_s$ carry all the dependencies with the site shape and, as LET is a macroscopic concept, it should not depend on this site shape. This dependency for the segment length is straightforward. In the case of the straggling effect, as the energy imparted per collision includes the energy transferred by secondary electrons, the site shape influences whether an electron with a given kinetic energy can leave the site or not. According to all discussed above, therefore, $\bar{L}_{\Delta,D,s}$ does not depend on the site shape but a spatial parameter given by the site diameter d. Furthermore, the term "restricted LET" refers to a spatial restriction of the energy imparted given by the parameter Δ, related somehow to the site diameter d, i.e. Δ=Δ(d), and it is relevant in those cases in which secondary electrons have ranges higher or comparable to d. On the other hand, the term "segment-averaged LET" refers to a longitudinal averaging of the energy imparted given by the mean segment length, $\bar{s}(d)$. In this case, this becomes important when LET changes significantly along that track segment.

The adequate values for the parameters Δ(d) and $\bar{s}(d)$ should be related to different clinical endpoints and the effect of the distribution of energy imparted in certain biological structures on those endpoints. Therefore, it is desirable to have a tool to calculate spatial segment-averaged LET distributions for different sites in order to look for correlations between $\bar{L}_{\Delta,D,s}$ values and the studied endpoints. By studying if these correlations exist, the quality of a restricted LET based on a given dimension d as an indicator of some biological effect can be assessed. In other words, LET restriction may be considered to explain the relation between RBE and LET. This work introduces this degree of freedom and proposes how to handle it in order to find such correlations. The concepts of unrestricted and segment-averaged LET make this calculation expected to be different from the usual LET calculations published in literature, which employ a concept of LET based on the (unrestricted) electronic stopping power values for protons in water[12-15]. These differences are expected to occur both at the entrance region, where the restriction effect plays a role, and at the proximities of the Bragg peak, where the segment-averaging becomes relevant. In all cases, $\bar{L}_{\Delta,D,s}$ is expected to be lower than the $\bar{L}_D$ calculated by those methods.

Regarding the models proposed in this work, a remarkable agreement between the analytical functions and the MC-based data can be found in FIGS. 3-7. This provides a double advantage: (i) calculations of $\bar{L}_{\Delta,D,s}$ values can be performed much faster than MC simulations by following this approach, since simple analytical functions are only used; and (ii) precision comparable to MC calculations, which resolves some of the issues of the current analytical models for LET calculations[14,15], besides the restricted and segment-averaged characteristics, which, as discussed above, might link LET with clinical endpoint. For example, performing LET calculation with this approach does not need to account for primary and secondary protons separately, as many of previous works do[12-14]. As, according to equations (6-7), one may use the clinical beam spectral fluence φ(E) to convolve the presented models and to finally obtain the corresponding LET values, it is enough with calculating the contribution from the secondaries in terms of fluence instead of in terms of LET. This may represent a real advantage when calculating lateral distribution of LET, as they only depend on the lateral beam fluence.

To perform clinical calculations of $\bar{L}_{\Delta,D,s}$ using the proposed method, each domain has to have a single value of $\bar{L}_{\Delta,D,s}$ which is obtained by averaging the modeled quantities respect to the spectral fluence of the beam, as shown in equations (6-7), i.e. by considering the distribution of entrance proton energies into the domain. Because of this polyenergetic averaging process, discrepancies observed in FIGS. 8A-B and even in FIGS. 9A-B, which shows the prediction for site dimensions whose data has not been employed in the model process, will probably diffuse. This is especially likely for the high discrepancies in low energies since in the clinical situation, relatively broad spectra are present and usually several beams converge at the same point. This means that the fraction of protons with low energy becomes small, which makes the contribution of low-energy protons to the integrals used in equations (6-7) to be irrelevant.

This work does not aim at determining the spectral fluence employed in equations (6-7), which is a separated problem to be addressed in future works. It should be noticed that the actual accuracy of this methodology strongly depends on the accuracy of the determination of the spectral fluence. Essentially, this determination consists in transporting protons in the actual media they traverse, so that either calculations based on MC simulations or a fluence-based kernel can be employed. As a consequence, resolution of CT scans, for example, becomes an issue for this spectral fluence determination. However, the intrinsic microscopic distributions are carried by the disclosed models regardless how accurate the spectral fluence is. On the other hand, as the disclosed microdosimetric models represent the way in which energy is imparted to water, the $\overline{L}_{\Delta,D,s}$ calculated distributions are referred to water. This seems convenient considering that the usual way to report dosimetric distributions in radiation therapy is dose-to-water. The presence of non-homogeneities, therefore, affects the proton transport problem (at macroscopic scale) rather than the microdosimetric energy deposition.

Calculations in this work can be extended beyond the current highest proton energy simulated in Geant4-DNA, currently fixed at 100 MeV, in order to simulate protons at the full clinical energy range. However, the contribution of protons with energy higher than 100 MeV to the LET value is expected to be low. Additionally, if the calculation is restricted to the LET distribution in a tumor, those energies above 100 MeV do not have much relevance. Nonetheless, an appreciable change of behavior in LET at 100 MeV is not expected along the rest of the clinical energy ranges, so the model presented here could be extrapolated to higher energies with probable limited error. In any case, Monte Carlo calculations can be performed to confirm this.

Conclusions are provided as follows.

A new way of averaging LET for a particle beam, called segment-averaged LET, is added to the known operations of dose-averaging and restriction on LET. This is done in order to incorporate the effects produced by the variation of proton stopping power along microscopic biological structures. Additionally, the quantities to calculate this segment-averaged LET can be measured and modeled analytically from microdosimetric Monte Carlo simulations of monoenergetic beams. These analytical models allow fast calculations of segment-averaged dose-averaged restricted LET with non-significant deviations from calculations derived from MC simulations carried out with Geant4-DNA. From these results, a method to perform clinical calculations of distributions of LET over a patient based on MC calculations (e.g., which could also be performed with a different code) can be built in a straightforward way.

The present disclosure may relate to at least the following aspects.

Aspect 1. A method comprising, consisting of, or consisting essentially of: determining data indicative of a particle beam to apply to an object of interest; determining imaging data associated with the object of interest, wherein the imaging data comprises a plurality of voxels of data; determining, for each of a plurality of domains in a first voxel of the plurality of voxels, a plurality of distributions for characterizing interactions of particles of the particle beam with the corresponding domain, wherein the plurality of distributions comprises a first distribution indicative of energy imparted in a corresponding domain due to a particle traveling in the domain; determining, based on the plurality of distributions and for each of the plurality of domains, first data comprising energy imparted by the particle beam to the corresponding domain; and outputting, based on the first data, data associated with treatment of the object of interest by the particle beam.

Aspect 2. The method of Aspect 1, wherein the data associated with treatment comprises one or more of (1) a three-dimensional distribution of dose or (2) a linear energy transfer (e.g., a segment-averaged, restricted, and/or dose averaged linear energy transfer) for the particle beam, and further comprising adjusting a treatment plan based on one or more of the first data or the data associated with the treatment.

Aspect 3. The method of any one of Aspects 1-2, wherein the first data comprises one or more of a linear energy transfer imparted by the particle beam to the corresponding domain or a dose imparted by the particle beam to the corresponding domain.

Aspect 4. The method of any one of Aspects 1-3, wherein the particle beam comprises a plurality of protons at a plurality of corresponding energies.

Aspect 5. The method of any one of Aspects 1-4, wherein determining the plurality of distributions comprises using one or more simulations (e.g., or models) to generate the plurality of distributions.

Aspect 6. The method of any one of Aspects 1-5, wherein the plurality of distributions comprise a second distribution indicative of segment length of a particle path in the domain and a third distribution indicative of energy imparted in the domain due to a collision of a particle.

Aspect 7. The method of Aspect 6, wherein the segment length comprises the distance a particle of the particle beam is predicted to travel after entering the domain before coming to rest.

Aspect 8. The method of any one of Aspects 1-7, further comprising determining, for a proton energy of the particle beam and based on the plurality of distributions, an energetic kernel, wherein the energetic kernel comprises a first average of at least one of the plurality of distributions and a first variance of the at least one of the plurality of distributions.

Aspect 9. The method of Aspect 8, further comprising performing a first convolution of an energy fluence of the particle beam with the first average and a performing a second convolution of the energy fluence of the particle beam with the first variance, wherein the first data is determined based on the results of the first convolution and the second convolution.

Aspect 10. The method of any one of Aspects 1-9, wherein the data associated with treatment plan is based on a model that accounts for one or more of variations of linear energy transfer in a domain, variations of dose in a domain, variations of segment length of paths of particles entering a domain, or variations of whether particles come to rest in a domain, or variations in the number of collisions of a particle in a domain, or variations in an amount of energy imparted in a collision of a particle in a domain.

Aspect 11. A device comprising, consisting of, or consisting essentially of: one or more processors; and memory storing instructions that, when executed by the one or more processors, cause the device to: determine data indicative of a particle beam to apply to an object of interest; determine imaging data associated with the object of interest, wherein the imaging data comprises a plurality of voxels of data;

determine, for each of a plurality of domains in a first voxel of the plurality of voxels, a plurality of distributions for characterizing interactions of particles of the particle beam with the corresponding domain, wherein the plurality of distributions comprises a first distribution indicative of energy imparted in a corresponding domain due to a particle traveling in the domain; determine, based on the plurality of distributions and for each of the plurality of domains, first data comprising energy imparted by the particle beam to the corresponding domain; and output, based on the first data, data associated with treatment of the object of interest by the particle beam.

Aspect 12. The device of Aspect 11, wherein the instructions, when executed by the one or more processors, further cause the device to adjust a treatment plan based on one or more of the first data or the data associated with the treatment.

Aspect 13. The device of any one of Aspects 11-12, wherein the first data comprises one or more of a linear energy transfer imparted by the particle beam to the corresponding domain or a dose imparted by the particle beam to the corresponding domain.

Aspect 14. The device of any one of Aspects 11-13, wherein the particle beam comprises a plurality of protons at a plurality of corresponding energies.

Aspect 15. The device of any one of Aspects 11-14, wherein the instructions that, when executed by the one or more processors, cause the device to determine the plurality of distributions comprises instructions that, when executed by the one or more processors, cause the device to use one or more simulations to generate the plurality of distributions.

Aspect 16. The device of any one of Aspects 11-15, wherein the plurality of distributions comprise a second distribution indicative of segment length of a particle path in the domain and a third distribution indicative of energy imparted in the domain due to a collision of a particle. The second distribution may have at least a portion of the segment lengths being indicative of the particle coming to rest in the domain.

Aspect 17. The device of Aspect 16, wherein the segment length comprises the distance a particle of the particle beam is predicted to travel after entering the domain before coming to rest.

Aspect 18. The device of any one of Aspects 11-17, wherein the instructions, when executed by the one or more processors, further cause the device to determine, for a proton energy of the particle beam and based on the plurality of distributions, an energetic kernel, wherein the energetic kernel comprises a first average of at least one of the plurality of distributions and a first variance of the at least one of the plurality of distributions.

Aspect 19. The device of Aspect 18, wherein the instructions, when executed by the one or more processors, further cause the device to perform a first convolution of an energy fluence of the particle beam with the first average and perform a second convolution of the energy fluence of the particle beam with the first variance, wherein the first data is determined based on the results of the first convolution and the second convolution.

Aspect 20. A system comprising, consisting of, or consisting essentially of: a particle beam generator; and at least one processor communicatively coupled to the particle beam generator and configured to: determine data indicative of a particle beam to cause the particle beam generator to apply to an object of interest; determine imaging data associated with the object of interest, wherein the imaging data comprises a plurality of voxels of data; determine, for each of a plurality of domains in a first voxel of the plurality of voxels, a plurality of distributions for characterizing interactions of particles of the particle beam with the corresponding domain, wherein the plurality of distributions comprises a first distribution indicative energy imparted in a corresponding domain due to a particle traveling in the domain; determine, based on the plurality of distributions and for each of the plurality of domains, first data comprising an energy imparted by the particle beam to the corresponding domain; and output, based on the first data, data associated with treatment of the object of interest by the particle beam.

Figure 10:
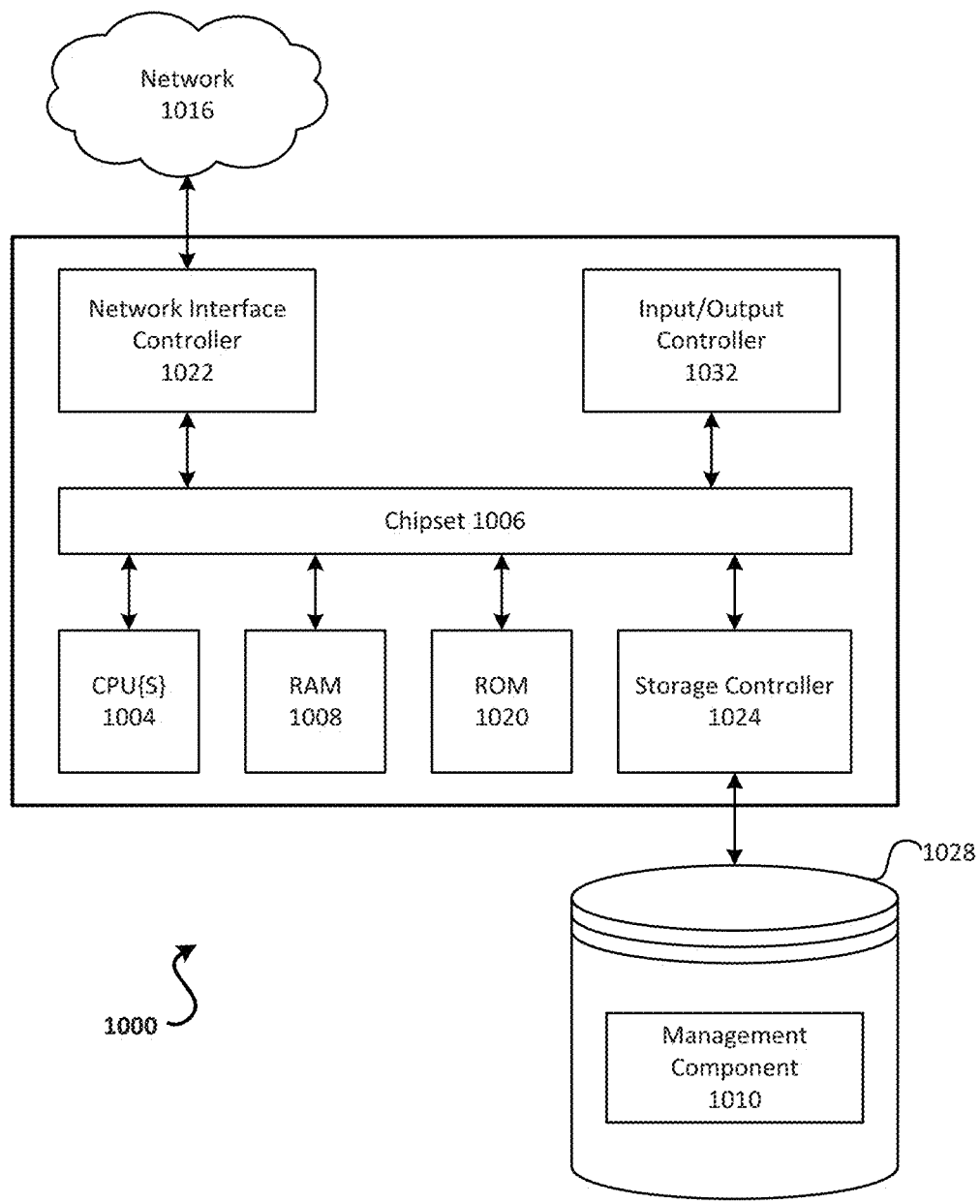
FIG. 10 is a block diagram illustrating an example computing device.

FIG. 10 depicts a computing device that may be used in various aspects, such as in treatment planning. The computer architecture shown in FIG. 10 shows a conventional server computer, workstation, desktop computer, laptop, tablet, network appliance, PDA, e-reader, digital cellular phone, or other computing node, and may be utilized to execute any aspects of the computers described herein, such as to implement the methods described herein.

The computing device 1000 may include a baseboard, or "motherboard," which is a printed circuit board to which a multitude of components or devices may be connected by way of a system bus or other electrical communication paths. One or more central processing units (CPUs) 1004 may operate in conjunction with a chipset 1006. The CPU(s) 1004 may be standard programmable processors that perform arithmetic and logical operations necessary for the operation of the computing device 1000.

The CPU(s) 1004 may perform the necessary operations by transitioning from one discrete physical state to the next through the manipulation of switching elements that differentiate between and change these states. Switching elements may generally include electronic circuits that maintain one of two binary states, such as flip-flops, and electronic circuits that provide an output state based on the logical combination of the states of one or more other switching elements, such as logic gates. These basic switching elements may be combined to create more complex logic circuits including registers, adders-subtractors, arithmetic logic units, floating-point units, and the like.

The CPU(s) 1004 may be augmented with or replaced by other processing units, such as GPU(s) 1005. The GPU(s) 1005 may comprise processing units specialized for but not necessarily limited to highly parallel computations, such as graphics and other visualization-related processing.

A chipset 1006 may provide an interface between the CPU(s) 1004 and the remainder of the components and devices on the baseboard. The chipset 1006 may provide an interface to a random access memory (RAM) 1008 used as the main memory in the computing device 1000. The chipset 1006 may further provide an interface to a computer-readable storage medium, such as a read-only memory (ROM) 1020 or non-volatile RAM (NVRAM) (not shown), for storing basic routines that may help to start up the computing device 1000 and to transfer information between the various components and devices. ROM 1020 or NVRAM may also store other software components necessary for the operation of the computing device 1000 in accordance with the aspects described herein.

The computing device 1000 may operate in a networked environment using logical connections to remote computing nodes and computer systems through local area network (LAN) 1016. The chipset 1006 may include functionality for providing network connectivity through a network interface controller (NIC) 1022, such as a gigabit Ethernet adapter. A NIC 1022 may be capable of connecting the computing device 1000 to other computing nodes over a network 1016.

It should be appreciated that multiple NICs 1022 may be present in the computing device 1000, connecting the computing device to other types of networks and remote computer systems.

The computing device 1000 may be connected to a mass storage device 1028 that provides non-volatile storage for the computer. The mass storage device 1028 may store system programs, application programs, other program modules, and data, which have been described in greater detail herein. The mass storage device 1028 may be connected to the computing device 1000 through a storage controller 1024 connected to the chipset 1006. The mass storage device 1028 may consist of one or more physical storage units. A storage controller 1024 may interface with the physical storage units through a serial attached SCSI (SAS) interface, a serial advanced technology attachment (SATA) interface, a fiber channel (FC) interface, or other type of interface for physically connecting and transferring data between computers and physical storage units.

The computing device 1000 may store data on a mass storage device 1028 by transforming the physical state of the physical storage units to reflect the information being stored. The specific transformation of a physical state may depend on various factors and on different implementations of this description. Examples of such factors may include, but are not limited to, the technology used to implement the physical storage units and whether the mass storage device 1028 is characterized as primary or secondary storage and the like.

For example, the computing device 1000 may store information to the mass storage device 1028 by issuing instructions through a storage controller 1024 to alter the magnetic characteristics of a particular location within a magnetic disk drive unit, the reflective or refractive characteristics of a particular location in an optical storage unit, or the electrical characteristics of a particular capacitor, transistor, or other discrete component in a solid-state storage unit. Other transformations of physical media are possible without departing from the scope and spirit of the present description, with the foregoing examples provided only to facilitate this description. The computing device 1000 may further read information from the mass storage device 1028 by detecting the physical states or characteristics of one or more particular locations within the physical storage units.

In addition to the mass storage device 1028 described above, the computing device 500 may have access to other computer-readable storage media to store and retrieve information, such as program modules, data structures, or other data. It should be appreciated by those skilled in the art that computer-readable storage media may be any available media that provides for the storage of non-transitory data and that may be accessed by the computing device 1000.

By way of example and not limitation, computer-readable storage media may include volatile and non-volatile, transitory computer-readable storage media and non-transitory computer-readable storage media, and removable and non-removable media implemented in any method or technology. Computer-readable storage media includes, but is not limited to, RAM, ROM, erasable programmable ROM ("EPROM"), electrically erasable programmable ROM ("EEPROM"), flash memory or other solid-state memory technology, compact disc ROM ("CD-ROM"), digital versatile disk ("DVD"), high definition DVD ("HD-DVD"), BLU-RAY, or other optical storage, magnetic cassettes, magnetic tape, magnetic disk storage, other magnetic storage devices, or any other medium that may be used to store the desired information in a non-transitory fashion.

A mass storage device, such as the mass storage device 1028 depicted in FIG. 10, may store an operating system utilized to control the operation of the computing device 1000. The operating system may comprise a version of the LINUX operating system. The operating system may comprise a version of the WINDOWS SERVER operating system from the MICROSOFT Corporation. According to further aspects, the operating system may comprise a version of the UNIX operating system. Various mobile phone operating systems, such as IOS and ANDROID, may also be utilized. It should be appreciated that other operating systems may also be utilized. The mass storage device 1028 may store other system or application programs and data utilized by the computing device 1000.

The mass storage device 1028 or other computer-readable storage media may also be encoded with computer-executable instructions, which, when loaded into the computing device 1000, transforms the computing device from a general-purpose computing system into a special-purpose computer capable of implementing the aspects described herein. These computer-executable instructions transform the computing device 1000 by specifying how the CPU(s) 1004 transition between states, as described above. The computing device 1000 may have access to computer-readable storage media storing computer-executable instructions, which, when executed by the computing device 1000, may perform the methods described herein.

A computing device, such as the computing device 1000 depicted in FIG. 10, may also include an input/output controller 1032 for receiving and processing input from a number of input devices, such as a keyboard, a mouse, a touchpad, a touch screen, an electronic stylus, or other type of input device. Similarly, an input/output controller 1032 may provide output to a display, such as a computer monitor, a flat-panel display, a digital projector, a printer, a plotter, or other type of output device. It will be appreciated that the computing device 1000 may not include all of the components shown in FIG. 10, may include other components that are not explicitly shown in FIG. 10, or may utilize an architecture completely different than that shown in FIG. 10.

As described herein, a computing device may be a physical computing device, such as the computing device 1000 of FIG. 10. A computing node may also include a virtual machine host process and one or more virtual machine instances. Computer-executable instructions may be executed by the physical hardware of a computing device indirectly through interpretation and/or execution of instructions stored and executed in the context of a virtual machine.

It is to be understood that the methods and systems are not limited to specific methods, specific components, or to particular implementations. It is also to be understood that the terminology used herein is for the purpose of describing particular embodiments only and is not intended to be limiting.

As used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other components, integers or steps. "Exemplary" means "an example of" and is not intended to convey an indication of a preferred or ideal embodiment. "Such as" is not used in a restrictive sense, but for explanatory purposes.

Components are described that may be used to perform the described methods and systems. When combinations, subsets, interactions, groups, etc., of these components are described, it is understood that while specific references to each of the various individual and collective combinations and permutations of these may not be explicitly described, each is specifically contemplated and described herein, for all methods and systems. This applies to all aspects of this application including, but not limited to, operations in described methods. Thus, if there are a variety of additional operations that may be performed it is understood that each of these additional operations may be performed with any specific embodiment or combination of embodiments of the described methods.

As will be appreciated by one skilled in the art, the methods and systems may take the form of an entirely hardware embodiment, an entirely software embodiment, or an embodiment combining software and hardware aspects. Furthermore, the methods and systems may take the form of a computer program product on a computer-readable storage medium having computer-readable program instructions (e.g., computer software) embodied in the storage medium. More particularly, the present methods and systems may take the form of web-implemented computer software. Any suitable computer-readable storage medium may be utilized including hard disks, CD-ROMs, optical storage devices, or magnetic storage devices.

Embodiments of the methods and systems are described herein with reference to block diagrams and flowchart illustrations of methods, systems, apparatuses and computer program products. It will be understood that each block of the block diagrams and flowchart illustrations, and combinations of blocks in the block diagrams and flowchart illustrations, respectively, may be implemented by computer program instructions. These computer program instructions may be loaded on a general-purpose computer, special-purpose computer, or other programmable data processing apparatus to produce a machine, such that the instructions which execute on the computer or other programmable data processing apparatus create a means for implementing the functions specified in the flowchart block or blocks.

These computer program instructions may also be stored in a computer-readable memory that may direct a computer or other programmable data processing apparatus to function in a particular manner, such that the instructions stored in the computer-readable memory produce an article of manufacture including computer-readable instructions for implementing the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

The various features and processes described above may be used independently of one another, or may be combined in various ways. All possible combinations and sub-combinations are intended to fall within the scope of this disclosure. In addition, certain methods or process blocks may be omitted in some implementations. The methods and processes described herein are also not limited to any particular sequence, and the blocks or states relating thereto may be performed in other sequences that are appropriate. For example, described blocks or states may be performed in an order other than that specifically described, or multiple blocks or states may be combined in a single block or state. The example blocks or states may be performed in serial, in parallel, or in some other manner. Blocks or states may be added to or removed from the described example embodiments. The example systems and components described herein may be configured differently than described. For example, elements may be added to, removed from, or rearranged compared to the described example embodiments.

It will also be appreciated that various items are illustrated as being stored in memory or on storage while being used, and that these items or portions thereof may be transferred between memory and other storage devices for purposes of memory management and data integrity. Alternatively, in other embodiments, some or all of the software modules and/or systems may execute in memory on another device and communicate with the illustrated computing systems via inter-computer communication. Furthermore, in some embodiments, some or all of the systems and/or modules may be implemented or provided in other ways, such as at least partially in firmware and/or hardware, including, but not limited to, one or more application-specific integrated circuits ("ASICs"), standard integrated circuits, controllers (e.g., by executing appropriate instructions, and including microcontrollers and/or embedded controllers), field-programmable gate arrays ("FPGAs"), complex programmable logic devices ("CPLDs"), etc. Some or all of the modules, systems, and data structures may also be stored (e.g., as software instructions or structured data) on a computer-readable medium, such as a hard disk, a memory, a network, or a portable media article to be read by an appropriate device or via an appropriate connection. The systems, modules, and data structures may also be transmitted as generated data signals (e.g., as part of a carrier wave or other analog or digital propagated signal) on a variety of computer-readable transmission media, including wireless-based and wired/cable-based media, and may take a variety of forms (e.g., as part of a single or multiplexed analog signal, or as multiple discrete digital packets or frames). Such computer program products may also take other forms in other embodiments. Accordingly, the present invention may be practiced with other computer system configurations.

Figure 11A:
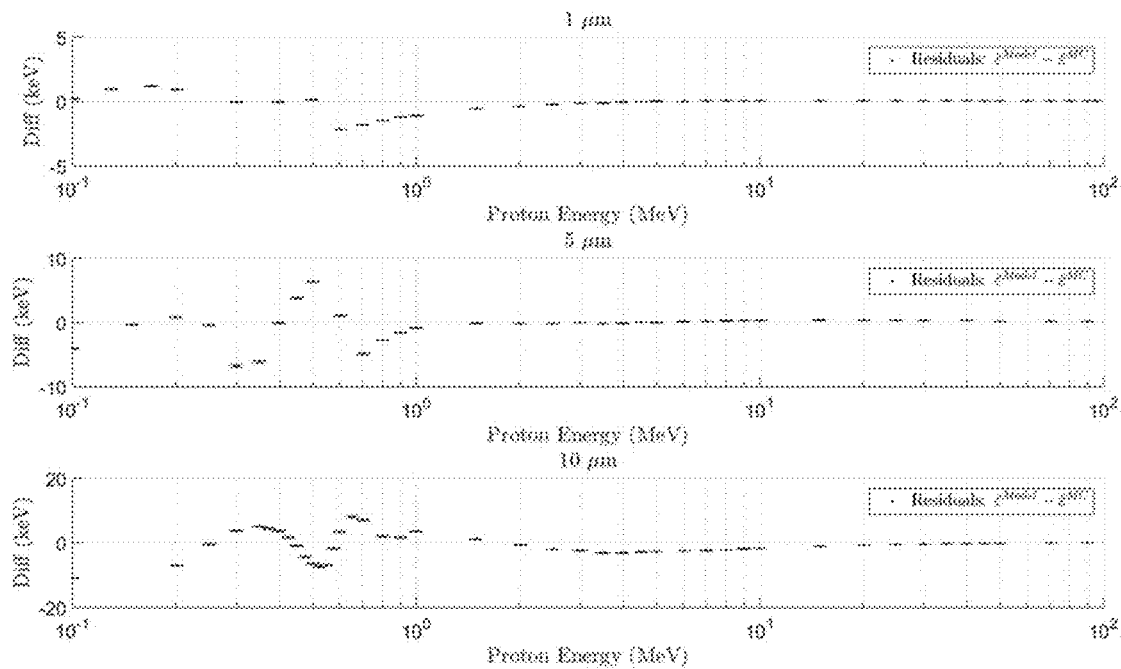
FIG. 11A shows residuals between MC-based and model-based calculations of average single-event energy imparted to the site.
Figure 11B:
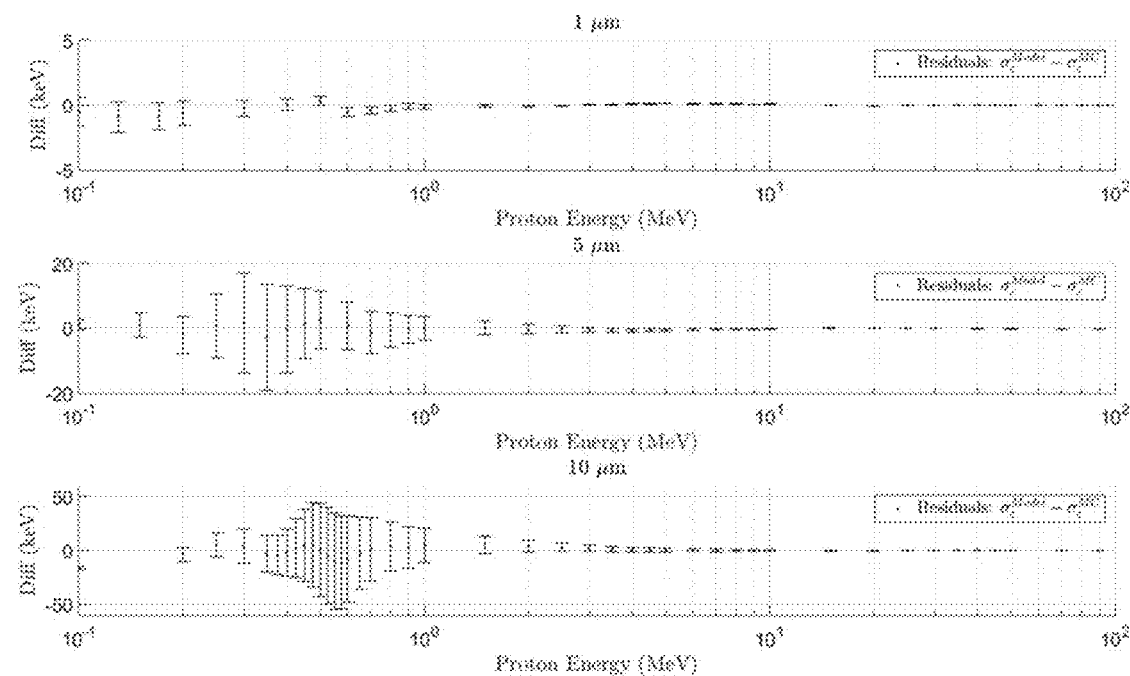
FIG. 11B shows residuals between MC-based and model-based calculations of the standard deviation of the corresponding distributions of energy imparted

FIGS. 11A-B show residuals for the fits of the functions in equations (9-10) to the data obtained from the MC simulations done with Geant4-DNA in liquid water for monoenergetic protons from 0.1 to 100 MeV for spherical sites with diameter of 1 μm, 5 μm and 10 μm, respectively. FIG. 11A shows average single-event energy imparted to the site. FIG. 11B shows the standard deviation of the corresponding distributions of energy imparted. Statistical uncertainties of the MC simulations (1σ) are shown with error bars.

FIGS. 12A-B shows residuals for the fitted functions to the calculations from MC simulations done with Geant4-

DNA in liquid water for monoenergetic protons from 0.01 to 100 MeV. FIG. 12A shows the average segment length for spherical sites with diameters of 1 μm, 5 μm and 10 μm, respectively. FIG. 12B shows the weighted-average segment length for spherical sites with diameters of 1 μm, 5 μm and 10 μm, respectively. Statistical uncertainties of the MC simulation (1σ) are shown with error bars.

FIG. 13 shows calculations from MC simulations done with Geant4-DNA in liquid water for monoenergetic protons from 0.01 to 100 MeV (points) and corresponding fitted function, equation (12) (lines) for the weighted-average segment length described in spherical sites with diameters of 1 μm, 5 μm and 10 μm, respectively. Statistical uncertainties of the MC simulation (1σ) are shown with error bars.

FIG. 14 shows residuals between the dose-mean lineal energy obtained from MC simulations of monoenergetic protons in liquid water done with Geant4-DNA and with our proposed analytical models by using equation (2), for spherical sites with diameters of 1 μm, 5 μm and 10 μm, respectively. Statistical uncertainties propagated from the MC simulations (1σ) are shown with error bars.

Figure 15A:
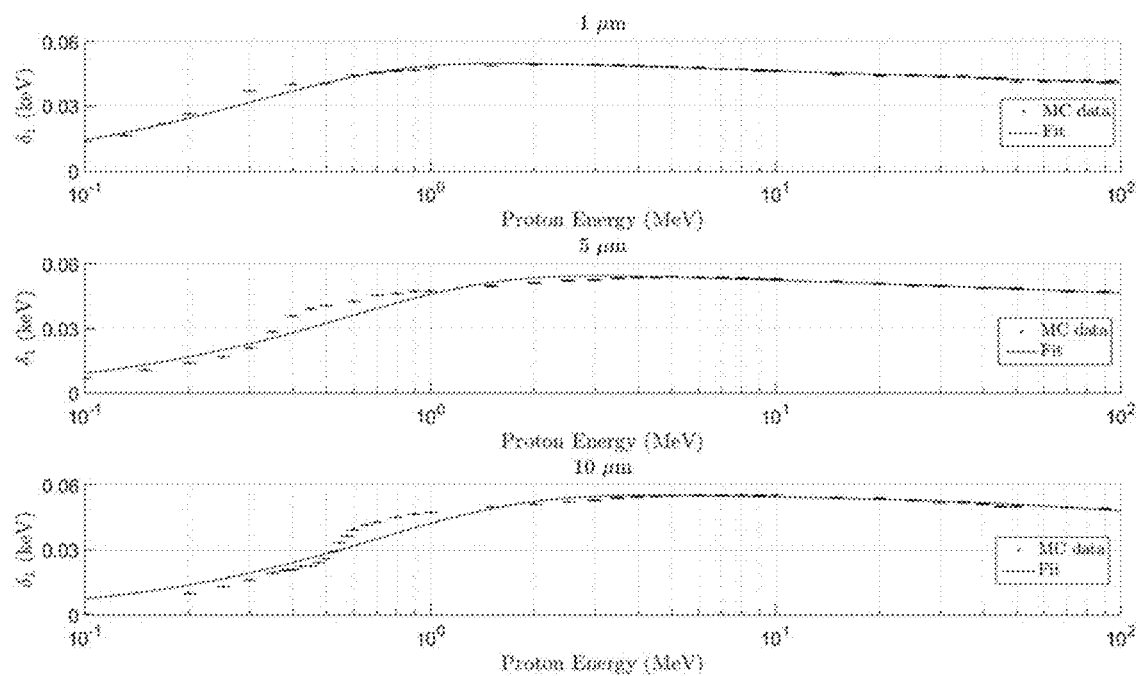
FIG. 15A shows calculations for the average of the distribution of energy imparted per collision in spherical sites with diameters of 1 μm, 5 μm and 10 μm, respectively.
Figure 15B:
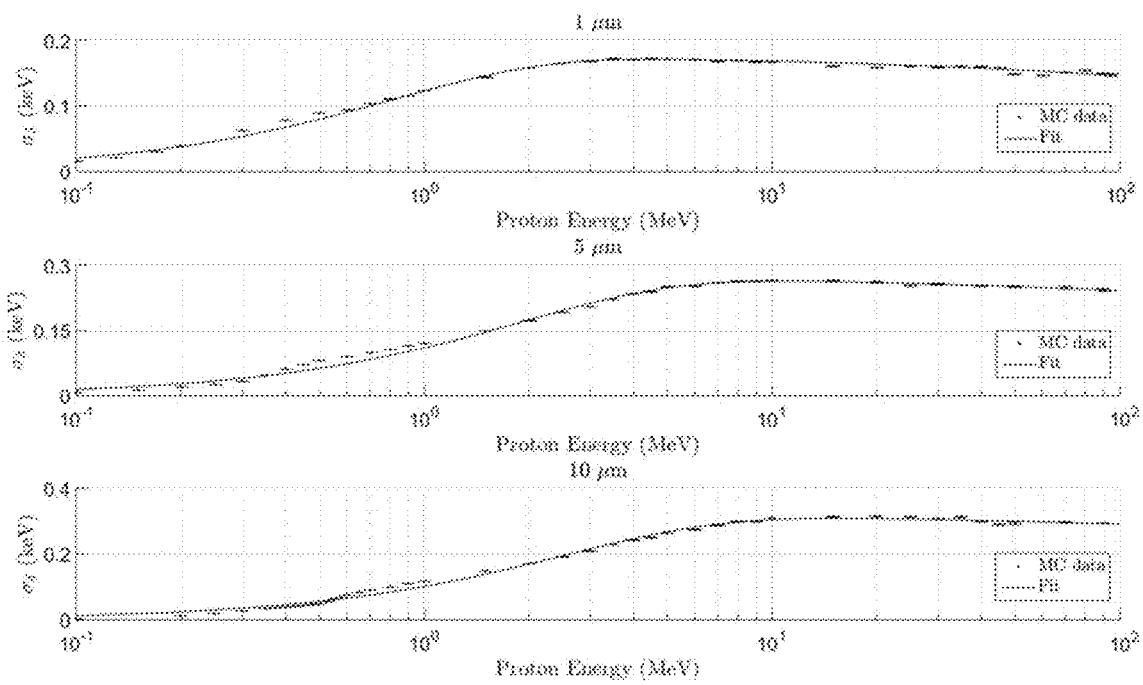
FIG. 15B shows the standard deviation of the distribution of energy imparted per collision in spherical sites with diameters of 1 µm, 5 µm and 10 µm, respectively

FIGS. 15A-B show calculations from Geant4-DNA MC simulations for monoenergetic protons in liquid water from 0.1 MeV to 100 MeV (points) and fitted function given in equation (11) (lines). FIG. 15A shows calculations for the average of the distribution of energy imparted per collision in spherical sites with diameters of 1 μm, 5 μm and 10 μm, respectively. FIG. 15B shows the standard deviation of the distribution of energy imparted per collision in spherical sites with diameters of 1 μm, 5 μm and 10 μm, respectively. Statistical uncertainties of the MC simulation (1σ) are shown with error bars.

Figure 16A:
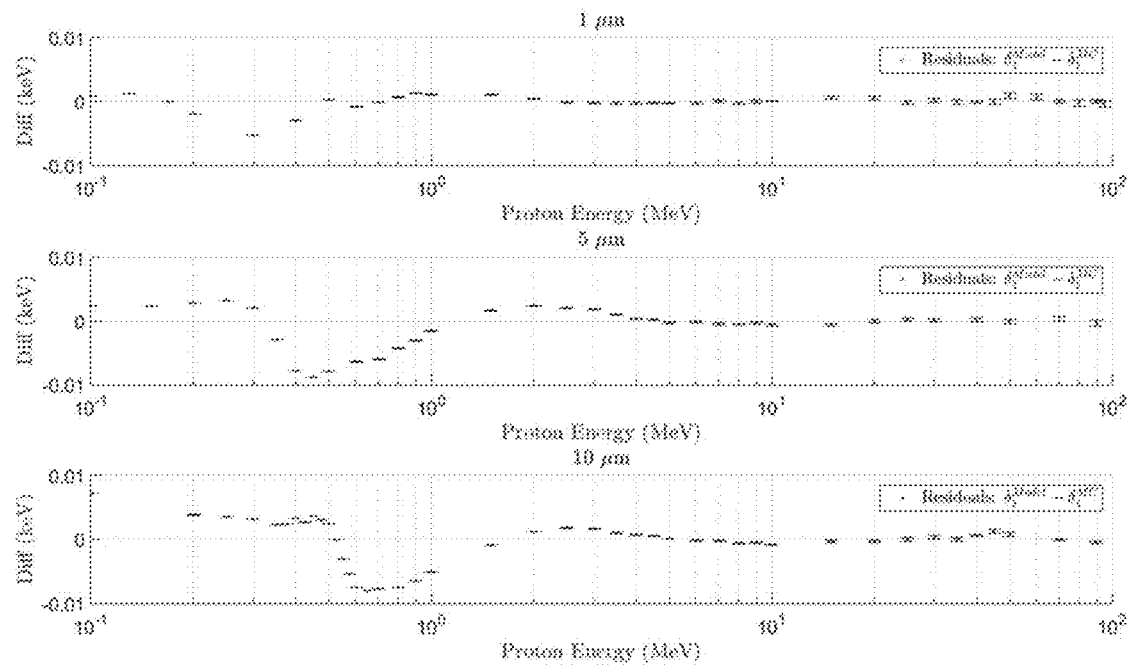
FIG. 16A shows residuals between MC-based and model-based calculations of average of the distribution of energy imparted per collision in spherical sites with diameters of 1 µm, 5 µm and 10 µm, respectively.
Figure 16B:
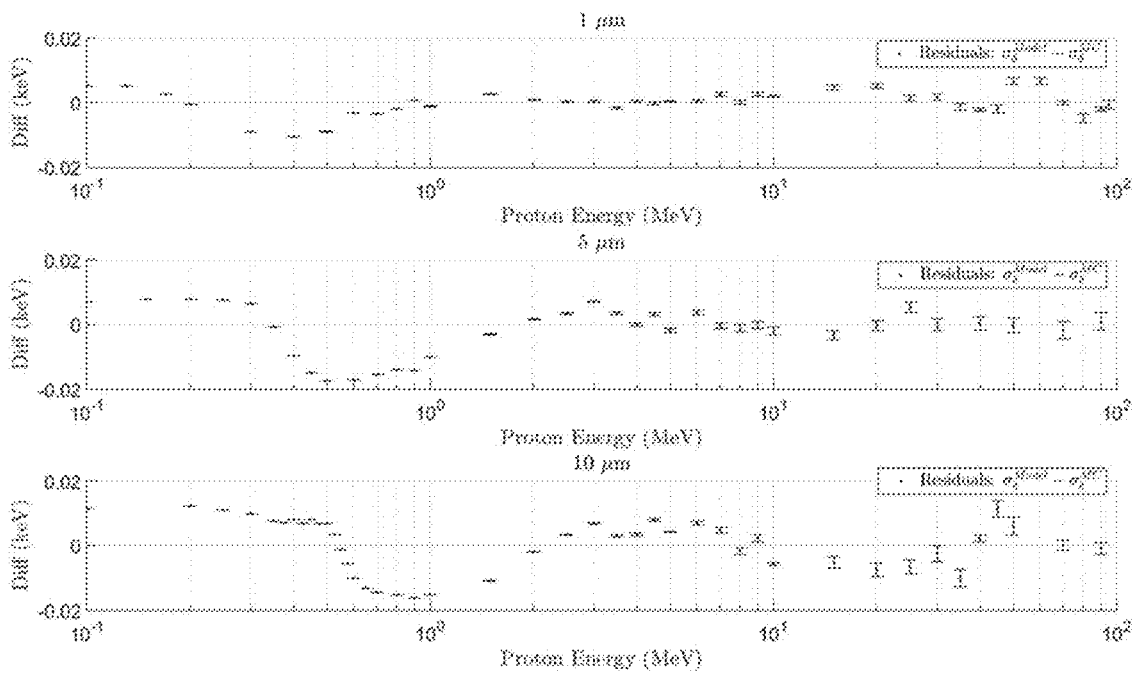
FIG. 16B shows residuals between MC-based and model-based calculations of standard deviation of the distribution of energy imparted per collision in spherical sites with diameters of 1 µm, 5 µm and 10 µm, respectively.
Figure 17:
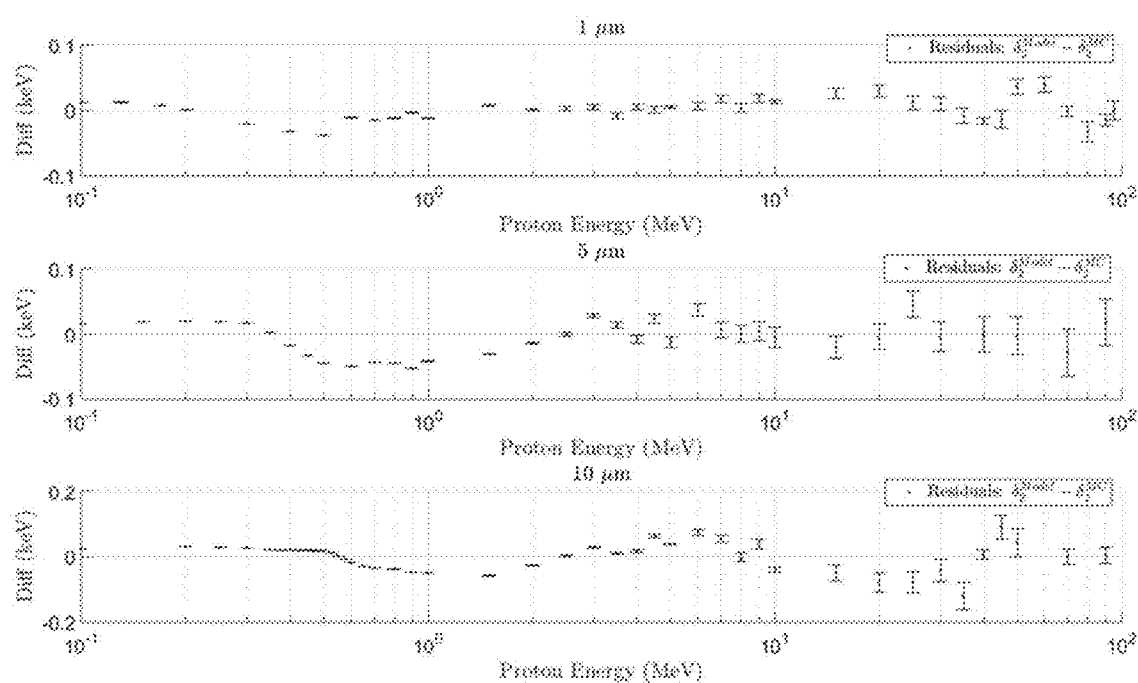
FIG. 17 shows residuals between the weighted average of the distribution of energy imparted per collision, $\delta_2$, calculated for monoenergetic protons in liquid water from Geant4-DNA MC simulations and from the analytical models described in equation (13) for spherical sites with diameters of 1 µm, 5 µm and 10 µm, respectively

FIGS. 16A-B show residuals for the fitted functions to the from Geant4-DNA MC simulations for monoenergetic protons in liquid water from 0.1 MeV to 100 MeV. FIG. 16A shows the average of the distribution of energy imparted per collision in spherical sites with diameters of 1 μm, 5 μm and 10 μm, respectively. FIG. 16B shows the standard deviation of the distribution of energy imparted per collision in spherical sites with diameters of 1 μm, 5 μm and 10 μm, respectively. Statistical uncertainties of the MC simulation (1σ) are shown with error bars.

FIG. 17 shows residuals between the weighted average of the distribution of energy imparted per collision, $\delta_2$, calculated for monoenergetic protons in liquid water from Geant4-DNA MC simulations and from the analytical models described in equation (13) for spherical sites with diameters of 1 μm, 5 μm and 10 μm, respectively. Statistical uncertainties of the MC simulations (1σ) are shown with error bars.

FIGS. 18A-B show differences between data obtained from the Geant4-DNA MC simulations of monoenergetic protons in liquid water and the prediction resulting from the interpolation of the fitting parameters of our models for spherical sites with diameter of 3 μm and 7 μm, respectively. FIG. 18A shows frequency-average of single-event energy imparted to the site, T. FIG. 18B shows segment-averaged dose-averaged restricted LET $L_{\Delta,D,s}$. Statistical uncertainties propagated from the MC simulations (1σ) are shown with error bars.

While the methods and systems have been described in connection with preferred embodiments and specific examples, it is not intended that the scope be limited to the particular embodiments set forth, as the embodiments herein are intended in all respects to be illustrative rather than restrictive.

It will be apparent to those skilled in the art that various modifications and variations may be made without departing from the scope or spirit of the present disclosure. Other embodiments will be apparent to those skilled in the art from consideration of the specification and practices described herein. It is intended that the specification and example figures be considered as exemplary only, with a true scope and spirit being indicated by the following claims.

REFERENCES

1. Grassberger C, Paganetti H. Elevated LET components in clinical proton beams. *Phys Med Biol*. 2011; 56(20):6677-6691. doi:10.1088/0031-9155/56/20/011
2. Paganetti H. Relative biological effectiveness (RBE) values for proton beam therapy. Variations as a function of biological endpoint, dose, and linear energy transfer. *Phys Med Biol*. 2014; 59(22):R419-R472. doi:10.1088/0031-9155/59/22/R419
3. Belli M, Cera F, Cherubini R, et al. RBE-LET relationships for cell inactivation and mutation induced by low energy protons in V79 cells: Further results at the LNL facility. *Int J Radiat Biol*. 1998; 74(4):501-509. doi:10.10100/095530098141375
4. Peeler C R, Mirkovic D, Titt U, et al. Clinical evidence of variable proton biological effectiveness in pediatric patients treated for ependymoma. *Radiother Oncol*. 2016; 121(3):395-401. doi:10.1016/j.radonc.2016.11.001
5. Grün R, Friedrich T, Traneus E, Scholz M. Is the dose-averaged LET a reliable predictor for the relative biological effectiveness? *Med Phys*. 2018. doi:10.1002/mp.13347
6. Fager M, Toma-Dasu I, Kirk M, et al. Linear Energy Transfer Painting With Proton Therapy: A Means of Reducing Radiation Doses With Equivalent Clinical Effectiveness. *Int J Radiat Oncol*. 2015; 91(5):1057-1064. doi:10.1016/j.ijrobp.2014.12.049
7. Unkelbach J, Botas P, Giantsoudi D, Gorissen B L, Paganetti H. Reoptimization of Intensity Modulated Proton Therapy Plans Based on Linear Energy Transfer. *Int J Radiat Oncol Biol Phys*. 2016; 96(5):1097-1106. doi:10.1016/j.ijrobp.2016.08.038
8. Rossi H H, Zaider M. Microdosimetry and Its Applications. Springer; 1996.
9. Kellerer A M. Fundamentals of microdosimetry. In: Kase K R, Bjarngard B E, Attix F H, eds. *The Dosimetry of Ionization Radiation. Volume I*. Academic Press, Inc.; 1985:77-162.
10. Lindborg L, Waker A. Microdosimetry. Experimental Methods and Applications. CRC Press; 2017.
11. Kellerer A M, Chmelevsky D. Criteria for the Applicability of LET. *Radiat Res*. 1975; 63(2):226-234. doi:10.2307/3574148
12. Wilkens J J, Oelfke U. Analytical linear energy transfer calculations for proton therapy. *Med Phys*. 2003; 30(5):1006-815. doi:10.1118/1.1567852
13. Wilkens J J, Oelfke U. Three-dimensional LET calculations for treatment planning of proton therapy. *Z Med Phys*. 2004; 14(1):41-46. doi:10.1078/0939-3889-00191
14. Sanchez-Parcerisa D, Cortés-Giraldo M A, Dolney D, Kondrla M, Fager M, Carabe A. Analytical calculation of proton linear energy transfer in voxelized geometries including secondary protons. *Phys Med Biol*. 2016; 61(4):1705-1721. doi:10.1088/0031-9155/61/4/1705
15. Marsolat F, De Marzi L, Pouzoulet F, Mazal A. Analytical linear energy transfer model including secondary particles: Calculations along the central axis of the proton pencil beam. *Phys Med Biol.* 2016; 61(2):740-757. doi: 10.1088/0031-9155/61/2/740
16. Xapsos M A. A Spatially Restricted Linear Energy Transfer Equation. *Radiat Res.* 1992; 132(3):282-287.
17. Chen J, Kellerer A M, Rossi H H. Radially restricted linear energy transfer for high-energy protons: a new analytical approach. *Radiat Environ Biophys.* 1994; 33(March):181-187.
18. Cucinotta F A, Nikjoo H, Goodhead D T. Model for Radial Dependence of Frequency Distributions for Energy Imparted in Nanometer Volumes from HZE Particles Model for Radial Dependence of Frequency Distributions for Energy Imparted in Nanometer Volumes from HZE Particles. *Radiat Res.* 2000; 153(4):459-468.
19. Rossi H H. Interpretation of Biological Response in Terms of Microdosimetry. *Ann NY Acad Sci.* 1969; 161 (1):260-271. doi:10.1111/j.1749-6632.1969.tb34064.x
20. ICRU. Report 36. Microdosimetry; 1983.
21. Hawkins R B. A Microdosimetric-Kinetic Model for the Effect of Non-Poisson Distribution of Lethal Lesions on the Variation of RBE with LET. *Radiat Res.* 2003; 160 (1):61-69. doi:10.1667/RR3010
22. Newhauser W D, Zhang R. The physics of proton therapy. *Phys Med Biol.* 2015; 60(8):R155-R209. doi: 10.1088/0031-9155/60/8/R155
23. Kellerer A. Considerations on the random traversal of convex bodies and solutions for general cylinders. *Radiat Res.* 1971; 47(2):359-376. doi:10.2307/3573243
24. Kellerer A M. Microdosimetry and Theory of Straggling. In: *Panel on Biophysical Aspects of Radiation Quality.*; 1968.
25. Kellerer A M. Chord-Length Distributions and Related Quantities for Spheroids. *Radiat Res.* 1984; 98(1):425-437.
26. Incerti S, Baldacchino G, Bernal M, et al. The Geant4-DNA project. *Int J Model Simulation, Sci Comput.* 2010; 1(2):157. doi:10.1142/S1793962310000122
27. Incerti S, Ivanchenko A, Karamitros M, et al. Comparison of GEANT4 very low energy cross section models with experimental data in water. *Med Phys.* 2010; 37(9): 4692-4708. doi:10.1118/1.3476457
28. Bernal M A A, Bordage M C C, Brown J M C M C, et al. Track structure modeling in liquid water: A review of the Geant4-DNA very low energy extension of the Geant4 Monte Carlo simulation toolkit. *Phys Medica.* 2015; 31(8):861-874. doi:10.1016/j.ejmp.2015.10.087
29. Incerti S, Kyriakou I, Bernal M A, et al. Geant4-DNA example applications for track structure simulations in liquid water: A report from the Geant4-DNA Project. *Med Phys.* 2018; 45(8):e722-e739. doi:10.1002/mp.13048
30. Bethe H. Zur Theorie des Durchgangs schneller Korpuskularstrahlen durch Materie. *Ann Phys.* 1930; 397(3): 325-400. doi:10.1002/and p.19303970303
31. ICRU. Report 73. Stopping of ions heavier than Helium. *J Int Comm Radiat Units Meas.* 2005; 5(1):iii-viii. doi: 10.1093/jicru/ndi002
32. Santa Cruz G A, Palmer M R, Matatagui E, Zamenhof R G. A theoretical model for event statistics in microsimetry. I: Uniform distribution of heavy ion tracks. *Med Phys.* 2001; 28(6):988-996. doi:10.1118/1.1376439
33. Ulmer W, Matsinos E. Theoretical methods for the calculation of Bragg curves and 3D distributions of proton beams. *Eur Phys J Spec Top.* 2010; 190(1):1-81. doi: 10.1140/epjst/e2010-01335-7
34. Berger M J, Coursey J S, Zucker M A, Chang J. Stopping-Power; Range Tables for Electrons, Protons, and Helium Ions|NIST. NIST Standard Reference Database 124. https://www.nist.gov/pml/stopping-power-range-tables-electrons-protons-and-helium-ions. Published 2017. Accessed Dec. 19, 2018.
35. The MathWorks Inc. Matlab R2018a and Curve Fitting toolbox. 2018.

What is claimed:
1. A method comprising:
determining data indicative of a particle beam to apply to an object of interest;
determining imaging data associated with the object of interest, wherein the imaging data comprises a plurality of voxels of data;
determining, for each of a plurality of domains in a first voxel of the plurality of voxels, a plurality of distributions for characterizing interactions of particles of the particle beam with the corresponding domain, wherein the plurality of distributions comprises a first distribution comprising an energy value imparted in a corresponding domain due to a particle traveling in the domain;
determining, based on at least the first distribution, an analytical function that models at least the first distribution;
determining, based on the analytical function and for each of the plurality of domains, first data comprising energy imparted by the particle beam to the corresponding domain; and
outputting, based on the first data, data associated with treatment of the object of interest by the particle beam.
2. The method of claim 1, wherein the data associated with treatment comprises one or more of (1) a three-dimensional distribution of dose or (2) a segment-averaged, restricted, dose averaged linear energy transfer for the particle beam, and further comprising adjusting a treatment plan based on one or more of the first data or the data associated with the treatment.
3. The method of claim 1, wherein the first data comprises one or more of a linear energy transfer imparted by the particle beam to the corresponding domain or a dose imparted by the particle beam to the corresponding domain.
4. The method of claim 1, wherein the particle beam comprises a plurality of protons at a plurality of corresponding energies.
5. The method of claim 1, wherein determining the plurality of distributions comprises using one or more simulations to generate the plurality of distributions.
6. The method of claim 1, wherein the plurality of distributions comprise a second distribution indicative of segment length of a particle path in the domain and a third distribution indicative of energy imparted in the domain due to a collision of a particle.
7. The method of claim 6, wherein the segment length comprises the distance a particle of the particle beam is predicted to travel after entering the domain before coming to rest.
8. The method of claim 1, wherein determining the analytical function comprises determining, for a proton energy of the particle beam and based on the plurality of distributions, an energetic kernel, wherein the energetic kernel comprises a first average of at least one of the plurality of distributions and a first variance of the at least one of the plurality of distributions.
9. The method of claim 8, further comprising performing a first convolution of an energy fluence of the particle beam with the first average and a performing a second convolution of the energy fluence of the particle beam with the first variance, wherein the first data is determined based on the results of the first convolution and the second convolution.

10. The method of claim 1, wherein the data associated with treatment plan is based on a model that accounts for one or more of variations of linear energy transfer in a domain, variations of dose in a domain, variations of segment length of paths of particles entering a domain, or variations of whether particles come to rest in a domain, or variations in the number of collisions of a particle in a domain, or variations in an amount of energy imparted in a collision of a particle in a domain.

11. A device comprising:
one or more processors; and
memory storing instructions that, when executed by the one or more processors, cause the device to:
determine data indicative of a particle beam to apply to an object of interest;
determine imaging data associated with the object of interest, wherein the imaging data comprises a plurality of voxels of data;
determine, for each of a plurality of domains in a first voxel of the plurality of voxels, a plurality of distributions for characterizing interactions of particles of the particle beam with the corresponding domain, wherein the plurality of distributions comprises a first distribution comprising an energy value imparted in a corresponding domain due to a particle traveling in the domain;
determine, based on at least the first distribution, an analytical function that models at least the first distribution;
determine, based on the analytical function and for each of the plurality of domains, first data comprising energy imparted by the particle beam to the corresponding domain; and
output, based on the first data, data associated with treatment of the object of interest by the particle beam.

12. The device of claim 11, wherein the instructions, when executed by the one or more processors, further cause the device to adjust a treatment plan based on one or more of the first data or the data associated with the treatment.

13. The device of claim 11, wherein the first data comprises one or more of a linear energy transfer imparted by the particle beam to the corresponding domain or a dose imparted by the particle beam to the corresponding domain.

14. The device of claim 11, wherein the particle beam comprises a plurality of protons at a plurality of corresponding energies.

15. The device of claim 11, wherein the instructions that, when executed by the one or more processors, cause the device to determine the plurality of distributions comprises instructions that, when executed by the one or more processors, cause the device to use one or more simulations to generate the plurality of distributions.

16. The device of claim 11, wherein the plurality of distributions comprise a second distribution indicative of segment length of a particle path in the domain and a third distribution indicative of energy imparted in the domain due to a collision of a particle.

17. The device of claim 11, wherein the instructions that, when executed by the one or more processors, cause the device to determine the analytical function comprise instructions, that when executed by the one or more processors cause the device to determine, for a proton energy of the particle beam and based on the plurality of distributions, an energetic kernel, wherein the energetic kernel comprises a first average of at least one of the plurality of distributions and a first variance of the at least one of the plurality of distributions.

18. The device of claim 17, wherein the instructions, when executed by the one or more processors, further cause the device to perform a first convolution of an energy fluence of the particle beam with the first average and perform a second convolution of the energy fluence of the particle beam with the first variance, wherein the first data is determined based on the results of the first convolution and the second convolution.

19. A system comprising:
a particle beam generator; and
at least one processor communicatively coupled to the particle beam generator and configured to:
determine data indicative of a particle beam to cause the particle beam generator to apply to an object of interest;
determine imaging data associated with the object of interest, wherein the imaging data comprises a plurality of voxels of data;
determine, for each of a plurality of domains in a first voxel of the plurality of voxels, a plurality of distributions for characterizing interactions of particles of the particle beam with the corresponding domain, wherein the plurality of distributions comprises a first distribution comprising an energy value imparted in a corresponding domain due to a particle traveling in the domain;
determine, based on at least the first distribution, an analytical function that models at least the first distribution;
determine, based on the analytical function and for each of the plurality of domains, first data comprising an energy imparted by the particle beam to the corresponding domain; and
output, based on the first data, data associated with treatment of the object of interest by the particle beam.

20. The method of claim 1, wherein determining the analytical function that models the at least one first distribution comprises determining one of more of a model of a mean of the first distribution or a model of a standard deviation of the first distribution.

* * * * *